(12) United States Patent
Steele et al.

(10) Patent No.: US 7,103,482 B2
(45) Date of Patent: Sep. 5, 2006

(54) INSPECTION SYSTEM AND APPARATUS

(75) Inventors: M. Brandon Steele, Decatur, GA (US); Jeffrey Alan Hawthorne, Decatur, GA (US); Chunho Kim, Duluth, GA (US); David C. Sowell, Atlanta, GA (US)

(73) Assignee: Qcept Technologies, Inc., Atlanta, GA (US)

(*) Notice: Subject to any disclaimer, the term of this patent is extended or adjusted under 35 U.S.C. 154(b) by 140 days.

(21) Appl. No.: 10/710,836

(22) Filed: Aug. 5, 2004

(65) Prior Publication Data
US 2005/0059174 A1   Mar. 17, 2005

Related U.S. Application Data

(63) Continuation-in-part of application No. 10/771,628, filed on Feb. 3, 2004, which is a continuation of application No. 10/631,469, filed on Jul. 29, 2003, now Pat. No. 6,957,154.

(60) Provisional application No. 60/444,504, filed on Feb. 3, 2003.

(51) Int. Cl.
G01B 5/28 (2006.01)
H01L 21/00 (2006.01)
B08B 6/00 (2006.01)

(52) U.S. Cl. .................... 702/35; 702/36; 438/12; 134/1.3

(58) Field of Classification Search ............... 702/35, 702/36; 324/765; 438/12, 200, 906; 134/1.2, 134/1.3
See application file for complete search history.

(56) References Cited

U.S. PATENT DOCUMENTS 4,166,974 A   9/1979   Vermeers (Continued)

FOREIGN PATENT DOCUMENTS

DD   297509 A5   1/1992

(Continued)

OTHER PUBLICATIONS

B Scruton and B.H. Blott, A High Resolution Probe for Scanning Electrostatic Potential Profiles Across Surfaces; Journal of Physics E: Scientific Instruments (May 1973), pp. 472-474; vol. 6, No. 5, Printed in Great Britain.

(Continued)

Primary Examiner—Bryan Bui
Assistant Examiner—Meagan S Walling
(74) Attorney, Agent, or Firm—Foley & Lardner LLP

(57) ABSTRACT

A method and system for identifying a defect or contamination on a surface of a material. The method and system involves providing a material, such as a semiconductor wafer, using a non-vibrating contact potential difference sensor to scan the wafer, generate contact potential difference data and processing that data to identify a pattern characteristic of the defect or contamination.

24 Claims, 42 Drawing Sheets

U.S. PATENT DOCUMENTS

| | | | |
|---|---|---|---|
| 4,295,092 | A | 10/1981 | Okamura |
| 4,481,616 | A | 11/1984 | Matey |
| 4,973,910 | A | 11/1990 | Wilson |
| 5,087,533 | A | 2/1992 | Brown |
| 5,136,247 | A | 8/1992 | Hansen |
| 5,214,389 | A | 5/1993 | Cao et al. |
| 5,217,907 | A | 6/1993 | Bulucea et al. |
| 5,218,362 | A | 6/1993 | Mayes et al. |
| 5,270,664 | A | 12/1993 | McMurtry et al. |
| 5,272,443 | A | 12/1993 | Winchip et al. |
| 5,278,407 | A | 1/1994 | Ikebe et al. |
| 5,293,131 | A | 3/1994 | Semones et al. |
| 5,315,259 | A | 5/1994 | Jostlein |
| 5,369,370 | A | 11/1994 | Stratmann et al. |
| 5,381,101 | A | 1/1995 | Bloom et al. |
| 5,460,684 | A | 10/1995 | Saeki et al. |
| 5,517,123 | A | 5/1996 | Zhao et al. |
| 5,546,477 | A | 8/1996 | Knowles et al. |
| 5,583,443 | A | 12/1996 | McMurtry et al. |
| 5,723,980 | A | 3/1998 | Haase et al. |
| 5,723,981 | A | 3/1998 | Hellemans et al. |
| 5,773,989 | A | 6/1998 | Edelman et al. |
| 5,974,869 | A | 11/1999 | Danyluk et al. |
| 5,977,788 | A | 11/1999 | Lagowski |
| 6,011,404 | A * | 1/2000 | Ma et al. .................... 324/765 |
| 6,037,797 | A | 3/2000 | Lagowski et al. |
| 6,091,248 | A | 7/2000 | Hellemans et al. |
| 6,094,971 | A | 8/2000 | Edwards et al. |
| 6,097,196 | A | 8/2000 | Verkuil et al. |
| 6,114,865 | A | 9/2000 | Lagowski et al. |
| 6,127,289 | A | 10/2000 | Debusk |
| 6,139,759 | A | 10/2000 | Doezema et al. |
| 6,198,300 | B1 | 3/2001 | Doezema et al. |
| 6,201,401 | B1 | 3/2001 | Hellemans et al. |
| 6,232,134 | B1 | 5/2001 | Farber et al. |
| 6,255,128 | B1 | 7/2001 | Chacon et al. |
| 6,265,890 | B1 | 7/2001 | Chacon et al. |
| 6,517,669 | B1 | 2/2003 | Chapman |
| 6,520,839 | B1 | 2/2003 | Gonzalez-Martin et al. |
| 6,538,462 | B1 | 3/2003 | Lagowski et al. |
| 6,546,814 | B1 | 4/2003 | Choe et al. |
| 6,551,972 | B1 | 4/2003 | Lei et al. |
| 6,597,193 | B1 | 7/2003 | Lagowski et al. |
| 6,664,546 | B1 | 12/2003 | McCord et al. |
| 6,664,800 | B1 | 12/2003 | Chacon et al. |
| 6,680,621 | B1 | 1/2004 | Savtchouk et al. |
| 6,717,413 | B1 | 4/2004 | Danyluk et al. |
| 2002/0140564 | A1 | 10/2002 | Danyluk et al. |
| 2002/0186036 | A1 | 12/2002 | Smith |
| 2003/0052374 | A1 | 3/2003 | Lee et al. |
| 2003/0129776 | A1 | 7/2003 | Eom et al. |
| 2003/0139838 | A1 | 7/2003 | Marella |
| 2003/0164942 | A1 | 9/2003 | Take |
| 2003/0175945 | A1 | 9/2003 | Thompson et al. |
| 2004/0029131 | A1 | 2/2004 | Thompson et al. |
| 2004/0057497 | A1 | 3/2004 | Lagowski et al. |
| 2004/0058620 | A1 | 3/2004 | Gotkis et al. |
| 2004/0105093 | A1 | 6/2004 | Hamamatsu et al. |
| 2004/0134515 | A1 | 7/2004 | Castrucci |

FOREIGN PATENT DOCUMENTS

| | | |
|---|---|---|
| EP | 1039227 | 9/2000 |
| EP | 1304463 | 4/2003 |
| WO | WO 01/90730 A2 | 11/2001 |

OTHER PUBLICATIONS

Yano D et al: "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

Castaldini A et al: "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Korach C S et al: "Measurement of perfluoropolyether lubricant thickness on a magnetic disk surface", Applied Physics Letters, American Institute of Physics, New York, NY, US; vol. 79, No. 5, Jul. 30, 2001, pp. 698-700, XP012029958, ISSN: 0003-6951 (p. 699, left column; fig. 2).

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Castaldini A et al: "Scanning Kelvin probe and surface photovoltage analysis of multicrystalline silicon", Materials Science and Engineering B., Elsevier Sequoia, Lausanne, CH; vol. 91-92, Apr. 30, 2002, pp. 234-238, XP004355534, ISSN: 0921-5107 (chapters 2.2 Scanning Kelvin probe: and "4.2 Scanning Kelvin probe analyses").

Lagel B et al: "A novel detection system for defects and chemical contamination in semiconductors based upon the scanning Kelvin probe", 14th International Vacuum Congress (IVC-14). 10th International Conference on Solid Surfaes (ICS-10). 5th International Conference on Nanometre-Scale Science and Technology (NANO-5). 10th International Conference on Quantitative Surface Analysis; vol. 433-435, pp. 622-626, XP002292441, Surface Science, Aug. 2, 1999, Elsevier, NL, ISSN: 003906028 (whole document).

Ren J et al: "Scanning Kelvin Microscope: a new method for surface investigations" 8. Arbeitstatgung Angewandte Oberflachenanalytik 'AOFA 8' ('Applied Surface Analysis'), Kaiserslautern, DE, Sep. 5-8, 1994; vol. 353, No. 3-4, pp. 303-306, XP009035181, Fresenius' Journal of Analytical Chemistry, Oct. 1995, Springer-Verlag, DE, ISSN: 0937-0633 (p. 304, right column; fig. 1).

Baumgartner H et al: "Micro Kelvin probe for local work-function measurements", Review of Scientific Instruments, May 1988, USA; vol. 59, No. 5, pp. 802-805, XP0022922442, ISSN: 0034-6748 (abstract; fig. 4, chapter "V. Results").

Danyluk S: "Non-vibrating contact potential imaging for semiconductor fabrication", Semicon West 2003, 'Online!, Jul. 14, 2003, pp. 1-15, XP002292443, retrieved from the internet: ,URL:http://dom.semi.org/web/wFiles.nsf/Lookup/TIS18_QceptTechnologiesInc/$file/TIS18%20QceptTechnologiesInc.Alternate.pdf. retrieved on Aug. 13, 2004 (whole document).

Reid, Jr., Lennox Errol, "Surface Characterization of Hard Disks Using Non-Contact Work Function Capacitance Probe," A Thesis Presented to the Academic Faculty in Partial Fulfillment of the Requirements for the Degree of Master of Science in Mechanical Engineering, Georgia Institute of Technology, Jun. 1986.

Moorman, M. et al., "A Novel, Micro-Contact Potential Difference Probe," Sensors and Actuators B, Elsevier Sequoia S.A., Lausanne, CH, vol. 94, No. 1.

* cited by examiner

INSPECTION SYSTEM AND APPARATUS

CROSS REFERENCE TO RELATED APPLICATIONS

This application is a continuation-in-part and claims priority from U.S. patent application Ser. No. 10/771,628, filed Feb. 3, 2004, which is itself a continuation of U.S. patent application Ser. No. 10/631,469, filed Jul. 29, 2003 now U.S. Pat. No. 6,957,154, which claims priority from U.S. Provisional Patent Application Ser. No. 60/444,504, filed Feb. 3, 2003.

FIELD OF THE INVENTION

The present invention is directed to methods and systems for the inspection of semiconductor wafers and other materials such as integrated circuits (IC) and any surface benefiting from inspection. Hereinafter, any material susceptible of surface inspection by the system herein described contact potential difference imaging device will be denoted generally as a "wafer". More particularly, the present invention is directed to a method and system for the characterization of microscopic and macroscopic defects through imaging and visualization of the contact potential difference topology on the wafer surface through the use of a non-vibrating contact potential difference sensor.

BACKGROUND OF THE INVENTION

The multi-billion dollar global market for semiconductor defect management is growing both in absolute terms and as a percentage of semiconductor capital equipment investment. In general, there are two factors that determine the economics of a semiconductor fabrication facility at a given utilization level, namely throughput and yield. As complex new technologies such as 300 mm wafers, copper interconnects, and reduced feature (circuit) sizes drive the margin of error in fabrication ever lower, new inspection technologies are critical to keep yields high and bottom-line economics attractive. Detection and elimination of chemical contamination and other types of defects is a constant concern for semiconductor manufacturers and equipment suppliers. Contamination can arise from use of processing chemicals, processing equipment, and poor handling techniques. Contaminants can include, for example, metals, carbon, and organic compounds. Other types of defects can result from a wide range of causes, including flaws in the semiconductor crystal, improper processing, improper handling, and defective materials. In addition, many cleaning steps are required in wafer fabrication, such as but not limited to the semiconductor industry. Each step is time consuming and requires expensive chemicals that may require special disposal procedures. Existing methods for monitoring or controlling these processes are expensive and time consuming. As a result, wafers are often cleaned for a longer period of time and using more chemicals than are required.

Defect detection and characterization systems can be divided into in-line and off-line systems. "In-line" refers to inspection and measurement that takes place inside the clean room where wafers are processed. "Off-line" refers to analysis that takes place outside of the wafer processing clean room, often in a laboratory or separate clean room that is located some distance from the manufacturing area. In addition, many of these analytical techniques are destructive, which requires either the sacrifice of a production wafer or the use of expensive "monitor" wafers for analysis.

In-line inspection and measurement is crucial for rapidly identifying and correcting problems that may occur periodically in the manufacturing process. A typical semiconductor wafer can undergo over 500 individual process steps and require weeks to complete. Each semiconductor wafer can have a finished product value of up to $100,000. Because the number of steps and period of time involved in wafer fabrication are so large substantial work in process can exist at any point in time. It is critical that process-related defects be found and corrected immediately before a large number (and dollar value) of wafers are affected. Such defects, regardless of the nature of the wafer, semiconductor, IC, or other device, are detrimental to performance and diminish productivity and profitability.

Many types of defects and contamination are not detectable using existing in-line tools, and these are typically detected and analyzed using expensive and time-consuming "off line" techniques (described below) such as Total Reflectance X-ray Fluorescence (TXRF), Vapor Phase Decomposition Inductively Coupled Plasma-Mass Spectrometry (VPD ICP-MS) or Secondary Ion Mass Spectrometry (SIMS). Since these techniques are used off-line (outside of the clean room used to process wafers) and usually occur hours, or even days, after the process step that has caused the contamination, their value is significantly limited.

A brief description of some well known techniques for wafer inspection and chemical contamination detection are presented in Table 1. This list is not in any sense exhaustive as there are a very large number of techniques that are used for some type of semiconductor analysis or characterization or for other surface inspection of other types of materials.

TABLE 1

| Analytical Technique | Description | In-line/Off-line |
|---|---|---|
| Total Reflection X-Ray Fluorescence (TXRF) | X-rays irradiate the wafer within the critical angle for total external reflectance, causing surface atoms to fluoresce. | Off-line |
| Automated Optical Microscopy | Optical images are acquired and automatically analyzed for detection of large defects. | In-line |
| Laser Backscattering | Wafer surface is illuminated with laser spots and the angle and/or polarization of reflected light is analyzed to detect and classify particles. | In-line |
| Vapor Phase Decomposition Inductively Coupled-Mass Spectrometry (VPD ICP-MS) | Wafers "scanned" with a drop of HF that is analyzed using mass spectrometry. | Off-line |
| Secondary Ion Mass Spectroscopy (SIMS) | Ion beam sputters the wafer surface creating secondary ions that are analyzed in a mass spectrometer. | Off-line |

Table 2 summarizes some major advantages and disadvantages of each example technique. In general, off-line detection techniques are extremely sensitive to tiny amounts of contamination; but such techniques are slow, expensive, and complex to operate. Some have limited, or no, imaging or surface mapping capability, or are destructive in nature. In-line techniques are much faster, non-destructive, and provide defect mapping, but have limited chemical contamination detection or analysis capability.

TABLE 2

| Analytical Technique | Advantages | Disadvantages |
| --- | --- | --- |
| Total Reflection X-Ray Fluorescence (TXRF) | Very sensitive<br>Some mapping capability<br>Nondestructive | Limited coverage<br>Unpatterned wafers only |
| Automated Optical Microscopy | Fast<br>Relatively low cost<br>Detects a wide range of macro defects (>50 microns)<br>Imaging of wafer surface<br>Non-contact/non-destructive | Very limited chemical and particle detection |
| Laser Backscattering | Fast<br>Relatively low cost<br>Detects very small particles<br>Imaging of water surface<br>Non-contact/non-destructive | Only detects particles - no chemistry |
| Vapor Phase Decomposition Inductively Coupled-Mass Spectrometry (VPD ICP-MS) | Very sensitive<br>Able to identify wide range of contaminants | Destructive<br>Slow<br>Expensive<br>Complex<br>Cannot image<br>Only works on bare silicon |
| Secondary Ion Mass Spectroscopy (SIMS) | Very sensitive<br>Detects a wide range of contaminants<br>Sub-surface detection | Expensive<br>Slow<br>Destructive |

In general, existing in-line wafer inspection tools operate at production speeds and generate images of the wafer surface that are processed to identify and locate defects. However, these techniques are, as mentioned above, very limited in their ability to detect chemical contamination. Laser backscattering systems are limited to detecting particles down to sub-micron sizes, and optical microscopy systems can only detect chemical contamination that results in a visible stain or residue. Both techniques lack the ability to identify or classify the chemical composition of the particle or contamination. Off-line laboratory techniques are used to qualify the cleanliness of new processes and equipment, or to analyze defects detected by in-line equipment or as part of failure analysis.

Another system that has been investigated is the use of Contact Potential Difference imaging (CPD). CPD refers to the electrical contact between two different metals and the electrical field that develops as a result of the differences in their respective maximum electronic energy level, i.e. their respective Fermi energies. When two metals are placed in contact, the Fermi energies of each will equilibrate by the flow of electrons from the metal with the lower Fermi energy to that of the higher. "Vibrating CPD sensor" refers to the vibration of one metal relative to the other in a parallel plate capacitor system. The vibration induces changes in the capacitance with time, and therefore a signal related with the surface profile. A CPD signal can also be generated by the translation of one surface past a reference sample through the use of a non-vibrating contact potential difference (nvCPD) sensor(s). This translation makes high speed scanning possible.

However, even these nvCPD sensors can themselves present certain difficulties. At a microscopic level, the surfaces of wafers are not flat due to wafer thickness variation, materials on the surface, "bowing", and other factors. In order to scan the wafer at a close but safe (i.e., close to the surface to promote good signal strength but far enough away to minimize any possibility of impacting the wafer surface) distance, an appropriate sensor height must be calculated and set. Thus, the height of the sensor above the wafer surface must be measured and controlled to produce repeatable results. Furthermore, height control is also necessary to minimize the sensor height to improve resolution and signal strength. However, height is difficult to control and measure, as is the appropriate height for measurements on each specific wafer.

It is possible to use one of many commercially available height sensors to control the height of the nvCPD sensor above the wafer surface. This requires the expense of an additional sensor, and the added complexity of a calibration routine to determine the position of the nvCPD sensor tip relative to measurements made by the separate height sensor.

A related problem is the difficulty in establishing a point of reference for all distance measurements, including height, related to an nvCPD scan. A reference point is needed to produce useful measurement data for image production.

In some sensor systems, such as nvCPD sensors, it is necessary to separate the sharp peak signal from the other two components of the signal (low frequency signal and induced noise signals) to locate and measure the contaminated areas of a wafer. This is challenging because the sharp peak signal behaves like noise, i.e., it consists of sharp peaks that alternate their polarity in high frequency mode. Because of this, conventional high frequency filters based only on the frequency domain do not work, as they would degrade the sharp peak signal significantly along with the noise.

In addition, an nvCPD signal is generally delayed in time, which impacts on the quality of the nvCPD signal/image. As the sampling time increases, the time delay becomes larger. The time delay may be explained by the equivalent RC circuit modeling the electrical signal path from the probe tip to the output of the A/D converter through the amplifier, the data acquisition board and the connecting lines between them. The equivalent capacitance is mixed with the capacitance between the probe and the wafer surface, the parasitic capacitance of the connecting lines, the internal capacitance of the amplifier, and other known conventional effects. The result is that minute feature signals are less detectable, and the signal magnitude and thus the signal-to-noise ratio are smaller.

Furthermore, topographical features of a wafer often produce a weak signal in comparison to the signals from chemical features. As the usefulness of topographical versus chemical features often varies depending on the particular circumstances of an imaging application, there exists a need to be able to amplify the signal indicating topographical features or to separate, superimpose, reduce or remove signal indicating chemical features.

Also, many different types of imaging systems currently rely on a chuck to spin a sample material, such a semiconductor wafer, relative to the probe apparatus. These current designs scan the sample surface at a constant rotational speed. The probe then scans the wafer by taking circumferential tracks of data at a constant sampling rate. Due to constant rotational speed and a constant sampling rate, it is apparent that the angular separation of an individual sample will be constant over the wafer surface. However, the actual physical spacing of the data in Cartesian coordinates varies with the radius of the track being scanned. In effect the data becomes denser as the radius decreases. In addition the amount of current generated in the sensor is a linear relationship with the relative speed of the probe to sample. The actual relative speed of the sample to the probe is then related to the radius of the track of data being collected so it is not a constant when the sample is scanned at a constant rotational speed. This results in signals of larger value on the outer radius of the sample and lowers the signal towards the center of the sample which results in higher signal to noise ratio than if data density were maintained at a substantially constant level.

In addition, a need exists to increase the overall accuracy, speed, and efficiency of current inspection systems. Current systems do not meet the increasing demand from the industry to provide a method of testing a wider variety of products in a more efficient and faster manner.

A critical need therefore exists for a fast, inexpensive, and effective means of detecting, locating, and classifying relatively small quantities of chemical content or features and physical features on wafers. In addition, there is a need for a system which minimizes cost and complexity of the sensor control mechanisms, such as height control. Furthermore, there is a need for methods and systems that have improved signal processing.

SUMMARY OF THE INVENTION

The present invention provides an inspection system that is a fast, inexpensive, and effective means of detecting, locating, and classifying relatively small quantities of chemical content, and physical features on materials, such as but not limited to semiconductor wafers, integrated circuit devices, liquid crystal display panels, or any material which may benefit from such inspections, while allowing for a minimization of the complexity of the sensor control mechanisms and an improvement in signal processing. In one exemplary embodiment, a wafer inspection system of the present invention includes steps for identifying a defect on a surface of a semiconductor wafer. In an exemplary embodiment, the steps comprise providing a semiconductor wafer; providing a non-vibrating contact potential difference sensor; scanning the semiconductor wafer relative to the non-vibrating contact potential difference sensor; generating contact potential difference data from the non-vibrating sensor; and processing the non-vibrating contact potential difference sensor data to automatically detect a pattern that is characteristic of a particular type of defect. A system in accordance with the principles of the present invention involves the relative motion of a probe and a testing material. In one embodiment, the probe is substantially stationary while the testing material is moved relative thereto, such as by spinning about an axis parallel with a sensing axis. In another embodiment, the probe is moved, such as by a rotational method or in a raster-type motion, relative to the substantially stationary testing material.

In addition, the system of the present invention provides, in an exemplary embodiment, a method for determining a reference point for the sensor. In addition, in some embodiments of the present invention the system includes a method for determining the height of the sensor. In addition, the present invention may preferably include a method for calculating the scan height to allow for static or dynamic wafer height variation. Furthermore, a system in accordance with the principles of the present invention preferably includes signal processing methods and devices for improving the native signal output of the sensor, such as by reducing noise, reducing signal time delay or applying various pattern recognition methodologies.

In another exemplary embodiment, the present invention relates to a method of biasing the system to provide for a stronger topographical signal in comparison to the chemical feature signal.

In another exemplary embodiment, the system of the present invention includes a mechanism to allow for substantially uniform data density. In one embodiment, the system includes a variable speed chuck that is able to compensate for the motion of the probe relative to the spinning surface of the material being inspected; thus allowing the data captured to have a substantially constant density.

In another exemplary embodiment, the system of the present invention comprises a plurality of probes. The plurality of probes may be configured to allow for different inspection scenarios, such as but not limited to using a linear or two-dimensional array.

DETAILED DESCRIPTION

Figure 1:
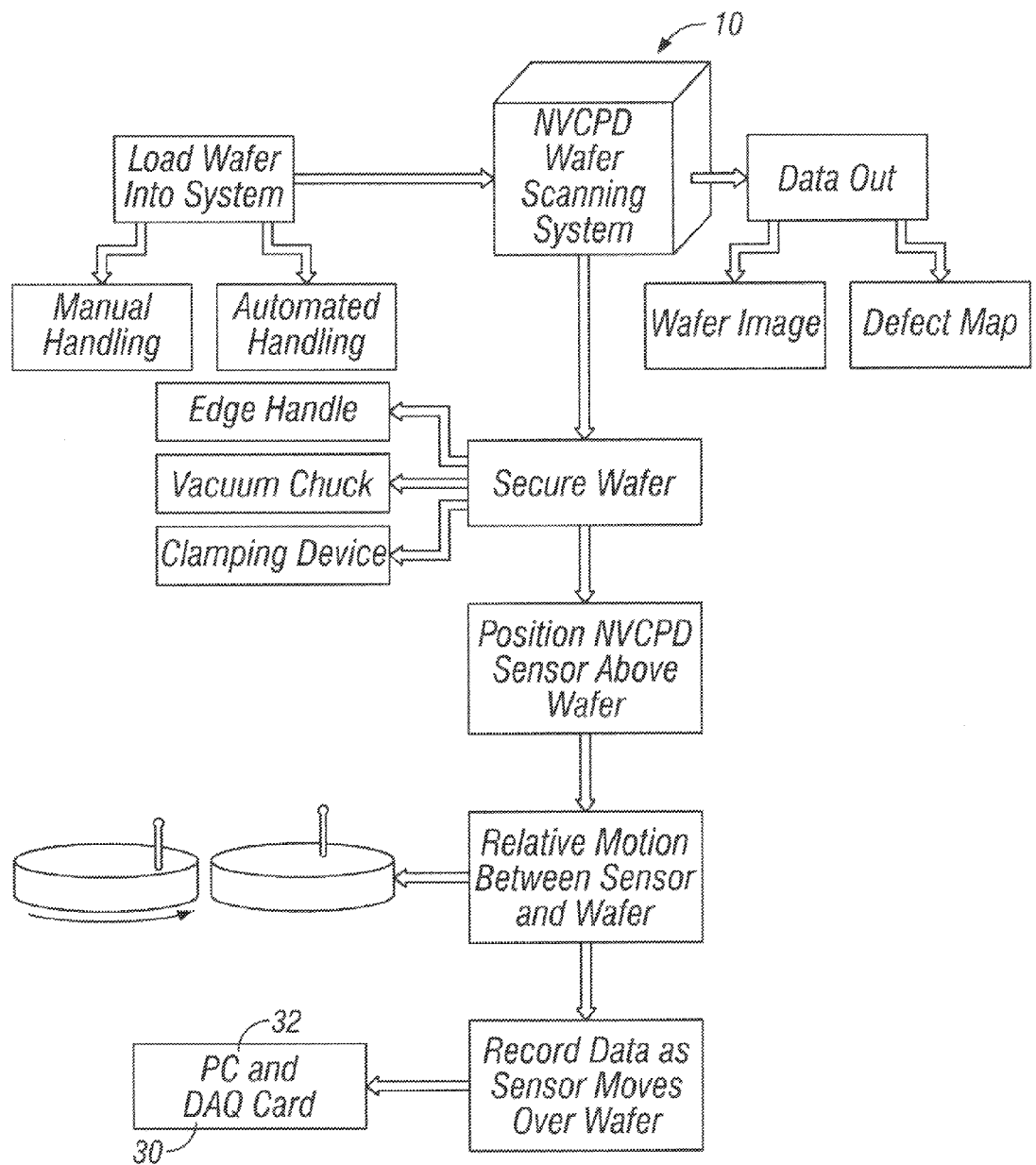
FIG. 1 illustrates one embodiment of the nvCPD scanning method and system.
Figure 2:
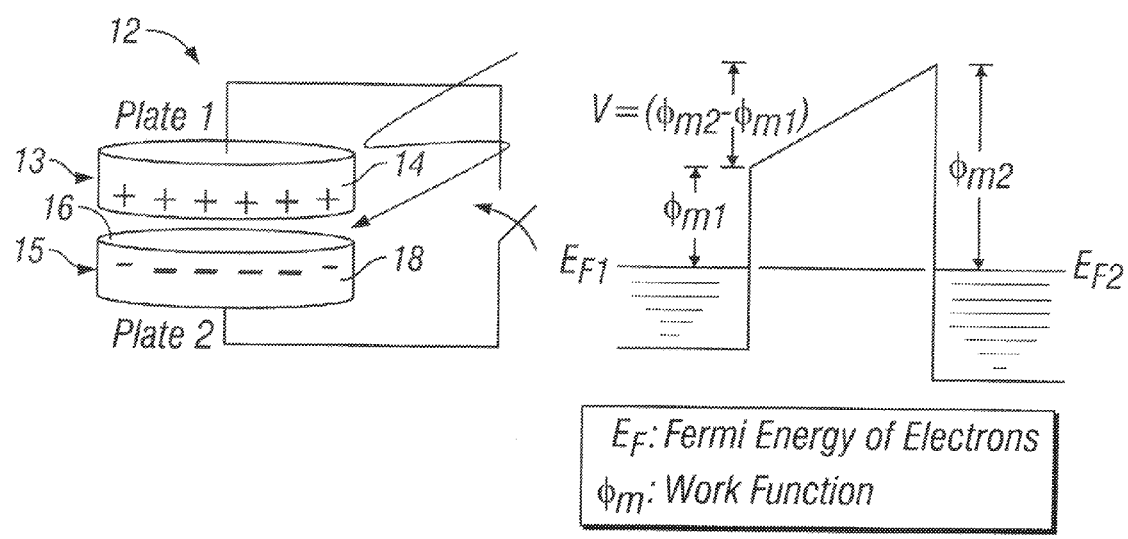
FIG. 2 illustrates the concept of the contact potential difference methodology.

A preferred embodiment of the invention is directed to an improved use of an nvCPD sensor. In particular, FIG. 1 illustrates a functional block flow diagram of components and operation of one preferred form of an nvCPD scanning system 10. A nvCPD sensor 12 (see FIG. 2) is based on the phenomena of contact potential difference which is a voltage generated between two dissimilar materials brought in close proximity to each other. An illustration of this concept can be seen in FIG. 2. In the case of the wafer scanning system 10, the sensor tip 13 forms a first plate 14 and a wafer 15 having a wafer surface 16 forms a second plate 18 (see FIG. 2.) Probe tip surface 20 of the first plate 14 is made of a conducting material with a fixed work function—generally, the difference in energy between the Fermi level of the solid and the free energy of the space outside the solid, including, in metals, the image potential of electrons just outside the surface. The wafer surface 16 of the second plate 18 has a work function which can vary due to irregularities in the semiconductor wafer surface 16 or contaminants or other materials deposited on the wafer surface 16. When the first plate 14 and the second plate 18 are electrically connected, the Fermi levels of the respective surface equilibrate and form an electric field between them. If the work function of the sensor tip 13 is fixed, the magnitude of the electric field is then related to the distance between the first plate 14 and the second plate 18, the relative dielectric between the first plate 14 and the second plate 18 and the work function of the wafer surface 16. In practice the first plate 14 and the second plate 18 equilibrate rapidly providing little to measure. To provide a current flow that can be measured, some motion of the sensor tip 12 relative to the wafer surface 16 must be realized. In one embodiment, the nvCPD sensor 12 is moved over the surface at a substantially fixed distance and variations in the wafer surface 16 cause a current to flow.

Figure 3:
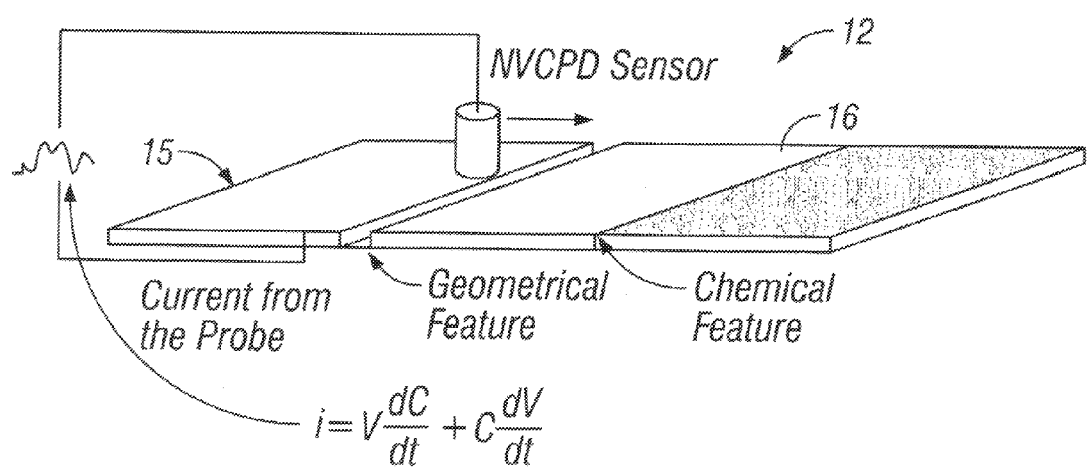
FIG. 3 illustrates an nvCPD scanning method.

An illustration of this concept can be seen in FIG. 3. The current flow from this nvCPD sensor 12 can be modeled by the following equation:

$$i = C\frac{\partial V}{\partial t} + V\frac{\partial C}{\partial t}$$

wherein C and V are defined as $$C = \frac{\varepsilon_0 \varepsilon_V A}{d} \text{ and } V = \frac{\Phi_{probe} - \Phi_{wafer}}{|e|}$$

and further wherein $\varepsilon_0$ is the permittivity of free space, $\varepsilon_r$ is the relative dielectric constant, A is the area of the probe tip, d is the distance between the sensor tip 13 and the wafer 15, $\phi$ is the work function of the respective surface, and e is the charge on an electron. The V term can also be described as a difference in surface potentials between the nvCPD sensor 12 and the wafer 15. In addition the surface potentials on the wafer surface 16 can vary due to defects. The overall surface potential is related to the underlying materials work function, but it can also be affected by adsorbed layers of material on the wafer surface 16. Even sub mono-layers of materials are known to significantly affect the surface potential.

Figure 4:
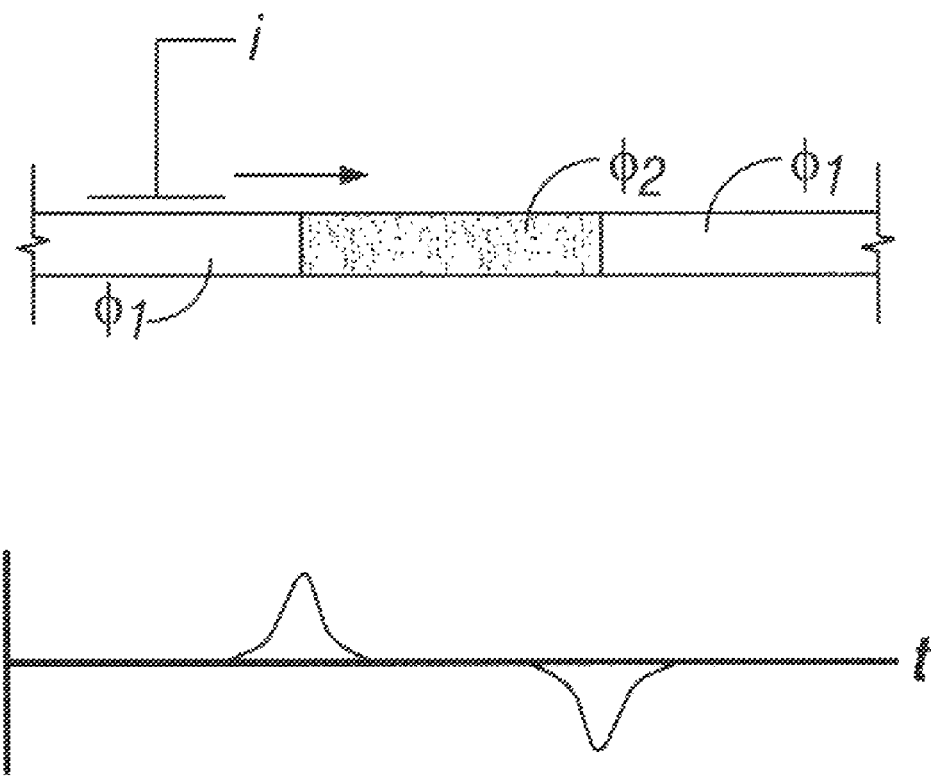
FIG. 4 illustrates the current output of an nvCPD probe as it passes over a positive and negative work function transition.

The $$C\frac{\partial V}{\partial t} \approx \frac{\Phi_{probe} - \Phi_{wafer}}{\Delta t}$$

term is related to changes in work function on the wafer surface 16. It can be seen that the magnitude of this term is related to the relative changes in work function on the wafer surface 16 and relative speed at which the nvCPD sensor 12 is moved over the wafer surface 16. An illustration of the signal generated from this can be seen in FIG. 4. Thus, a system in accordance with the principles of the present invention is capable of generating one-dimensional signals and two-dimensional images, although three-dimensional images can be generated.

Many defects can present themselves as variations in the wafer work function or the overall surface potential. Both chemical and physical (i.e., geographical) features of the wafer surface and the underlying materials can affect the work function of a particular portion or even a single point on the wafer surface; thus, these features can be detected by a sensor in accordance with the principles of the present invention. For instance, variation in semiconductor dopant concentrations in the wafer 15 will cause varying characteristic work functions. In addition, other materials that could diffuse into the wafer 15, such as but not limited to copper, will cause variations in work function. Within the semiconductor material (or any other material susceptible to measurement) itself, mechanical phenomena such as dislocation pile-ups, cracks, and scratches generate local stresses which will change the local work function. In addition, adsorbed layers of atomic or molecular contaminants even at the sub monolayer level will generate appreciable surface potential variations. Particles deposited on the wafer 16 with a surface potential different than the surrounding wafer material will also create a signal. Layers of chemicals commonly used in the wafer fabrication process will affect the surface potential of the wafer. For instance residual CMP slurry or photo-resist would cause local variations in surface potential detectable by the nvCPD sensor 12 of the present invention. Such defects and chemistry have associated with them characteristic signatures which enable inspection of the wafer surface.

The $$V\frac{\partial C}{\partial t}$$

term is related to changes in gap between the nvCPD sensor 12 and the wafer 15 or variations in the relative dielectric constant. Geometrical imperfections in the wafer surface 16 or particles on the wafer surface 16 would manifest themselves in this component. Also because of its differential nature, the magnitude of this component would also increase as the relative speed of the nvCPD sensor 12 to the wafer 15 is increased.

As previously mentioned, physical or geographical aspects and defects can be imaged using a system in accordance with the principles of the present invention. Many classes of wafer defects would appear as geometrical changes in the wafer surface 16. In the wafer 15 itself, surface cracks, scratches and etched trenches would be non-limiting examples of such defects causing a geometrical change in the wafer surface and an attendant change in the work function. In addition, particles deposited on the wafer 15 would also present themselves as a local change in the distance to the probe sensor tip 13.

Variations of dielectric films on the wafer 15 can also be detected. An example would be detecting variations in the oxide state grown on the silicon substrate (i.e. $SiO$, $SiO_2$, $SiO_3$, $SiO_4$). In addition, variations in dielectric of other non-conducting materials commonly deposited on the wafer could be detected.

It should also be noted that many features could present themselves as combinations of geometrical changes and chemical changes. For instance, a particle deposited on the wafer 15 of differing material than the underlying wafer 15 could cause variation. Also, a crack in the surface would also induce stresses that would cause variations in local work function.

Figure 5:
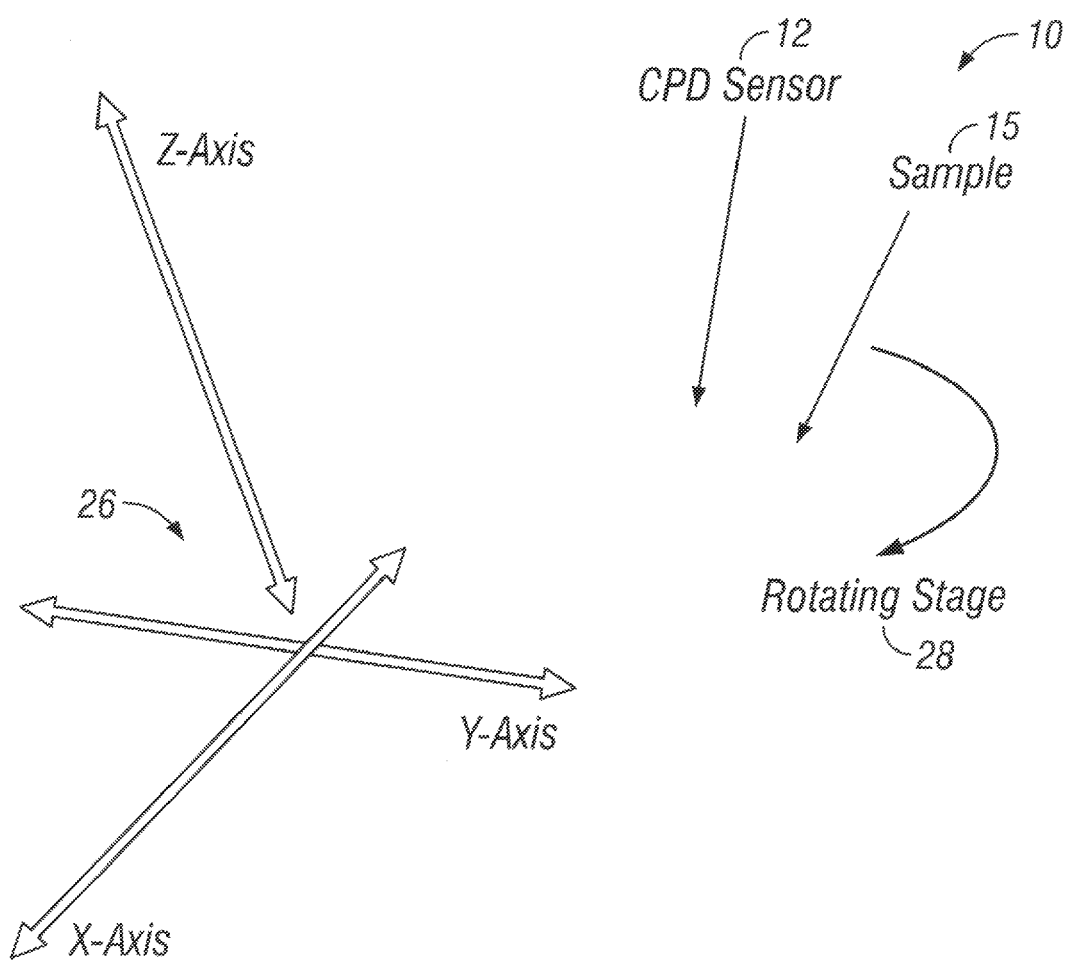
FIG. 5 illustrates axial orientation of the nvCPD system.
Figure 8A:
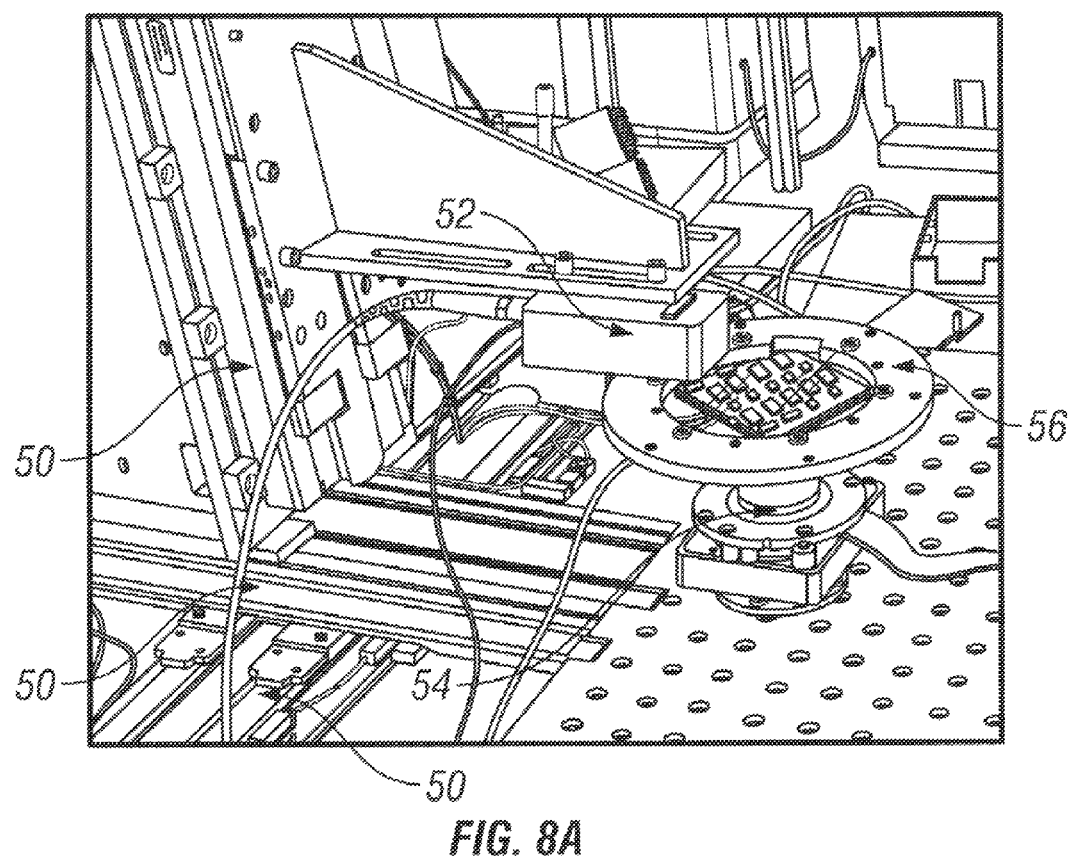
FIG. 8A illustrates one form of scanning nvCPD system with a three axis linear positioning system with the nvCPD sensor and a wafer mounted on a high speed spindle.
Figure 8B:
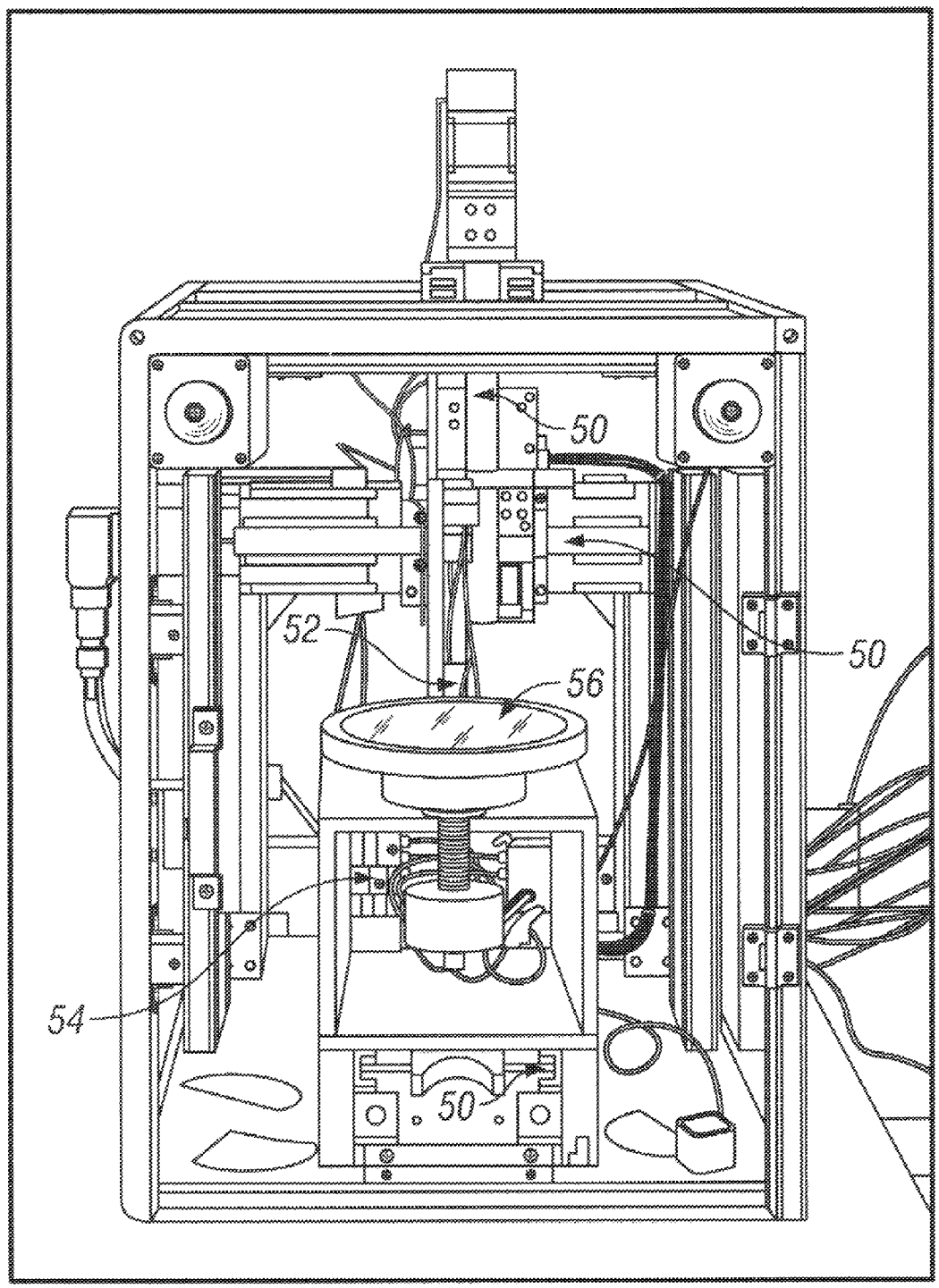
FIG. 8B illustrates another form of scanning nvCPD system.

In FIG. 5 is schematically shown one form of the system 10 for application of the nvCPD sensor 12 to scan the wafer 15 for defects and contamination. FIGS. 8A and 8B also illustrate more detailed drawings of two alternative operating embodiments of the system 10. The system 10 in FIG. 5 includes an X-Y-Z positioning system 26, a rotating wafer stage 28, a high speed data acquisition system 30 with a personal computer (PC) 32, and control software executed by the PC 32.

Figure 21A:
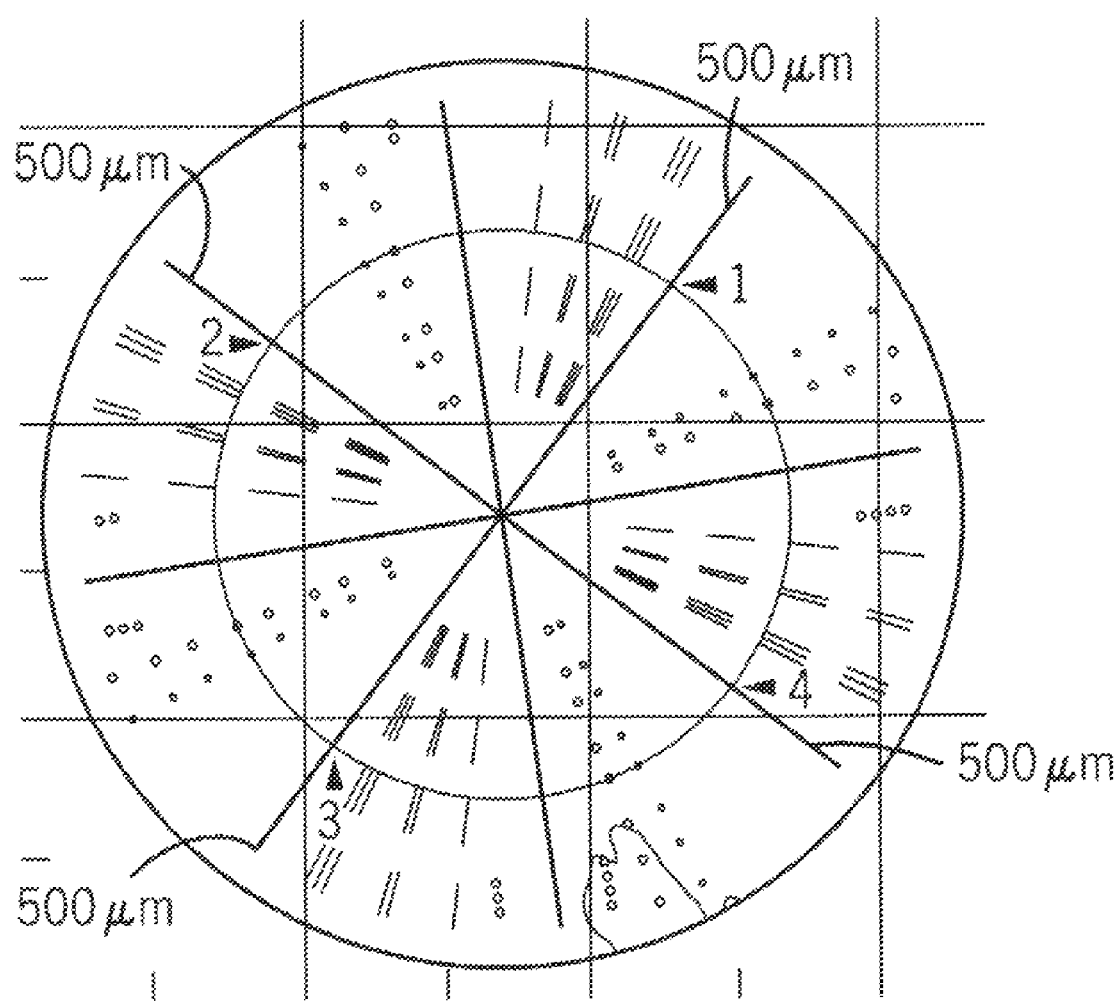
FIG. 21A illustrates a wafer map produced in accordance with the principles of the present invention, wherein the wafer pattern is one atomic layer thick over native silicon oxide.
Figure 21B:
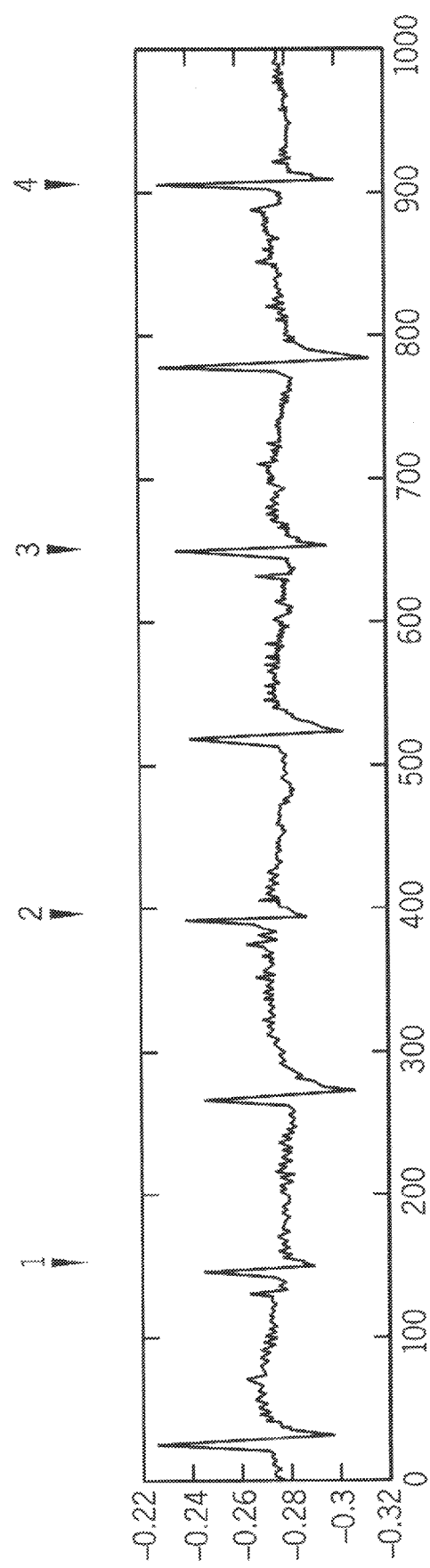
FIG. 21B is a graph showing signal strength along a single probe track.
Figure 21C:
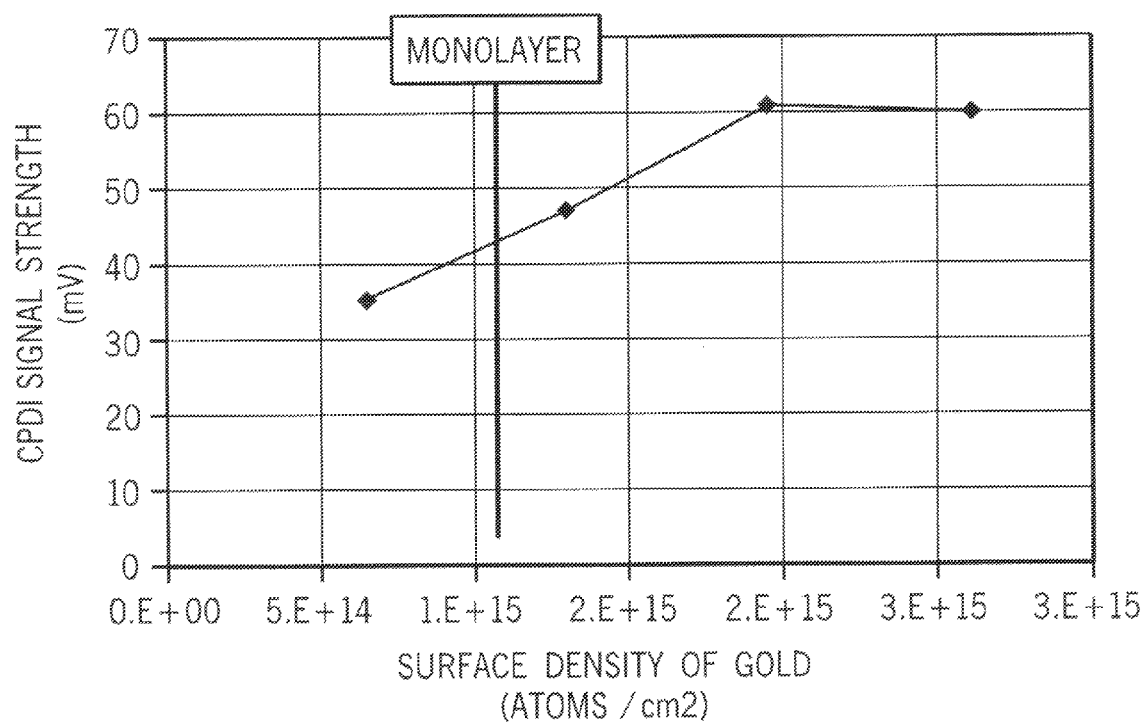
FIG. 21C is a graph of the signal strength versus the density of gold for the wafer map depicted in FIG. 21A.

As shown in more detail in FIG. 8A, in one embodiment, the wafer 15 is affixed to a rotating spindle or chuck 54 (see FIG. 1) using a clamping fixture 56 on the wafer edges. A sensor positioning system 50 includes an nvCPD sensor 52 positioned a fixed distance from the wafer 15 is mounted to a spindle 54. The wafer 15 (not seen in this view) is then rotated at high speed, and the nvCPD sensor 52 is translated radially to collect data in circumferential tracks. The scanning procedure as shown schematically in FIG. 9 lasts between a few seconds and several minutes, depending on the number of scanned tracks, the speed of the spindle 54, and the speed of the sensor positioning system 52. The tracks of data are then put together to form a CPD image. These CPD images allow the visualization of chemical and geometrical defects and thereby enable classification of the type of defect present on the wafer surface. Some examples of these CPD images can be seen in FIG. 10A–15 and are taken from a 100 mm wafer compared with optical images of the same wafer (see, Example infra). The present invention is capable of generating image maps of one atomic layer thick patterns, as shown in FIG. 21A. FIG. 21B illustrates the signal strength as the wafer is rotated relative to the probe, thus passing over defects and features of the wafer surface. As shown in FIG. 21C, the present invention, in fact, detected sputtered gold at densities less than a single complete atomic layer.

Figure 6:
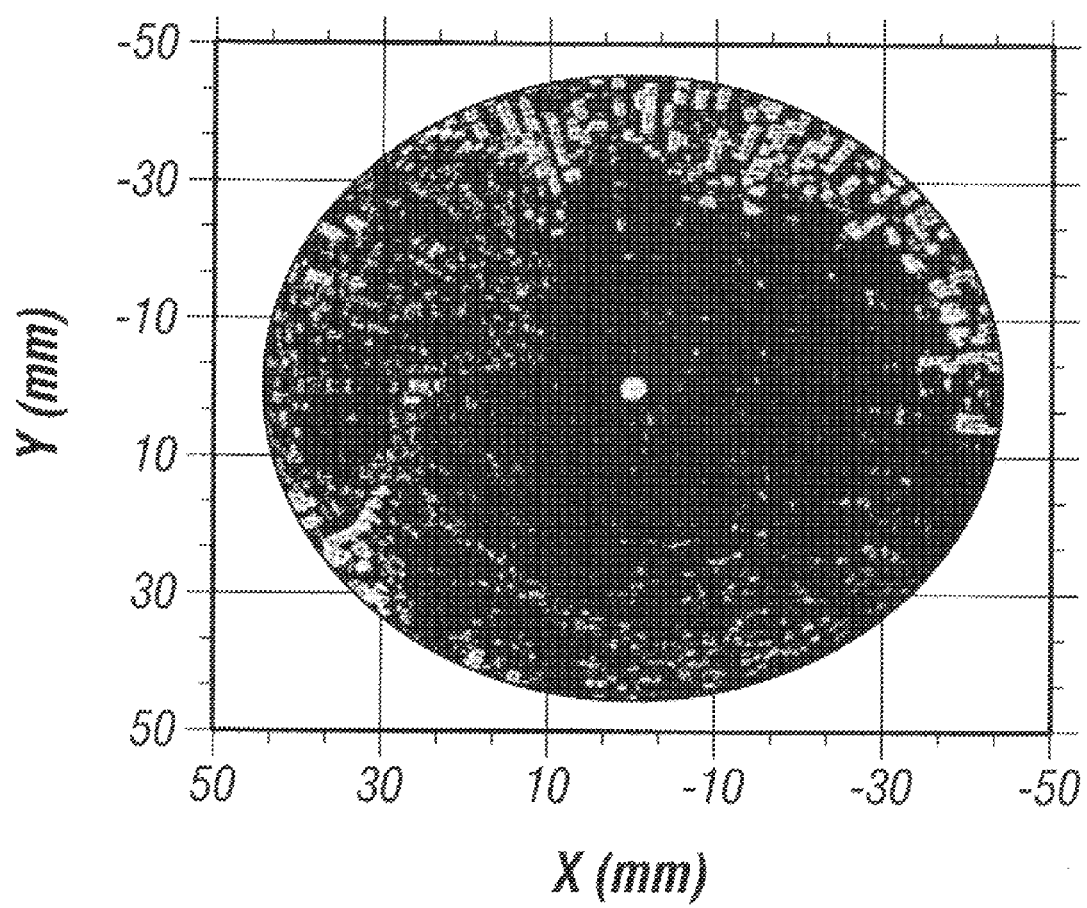
FIG. 6 illustrates standard deviation of signals within a scan area.
Figure 9:
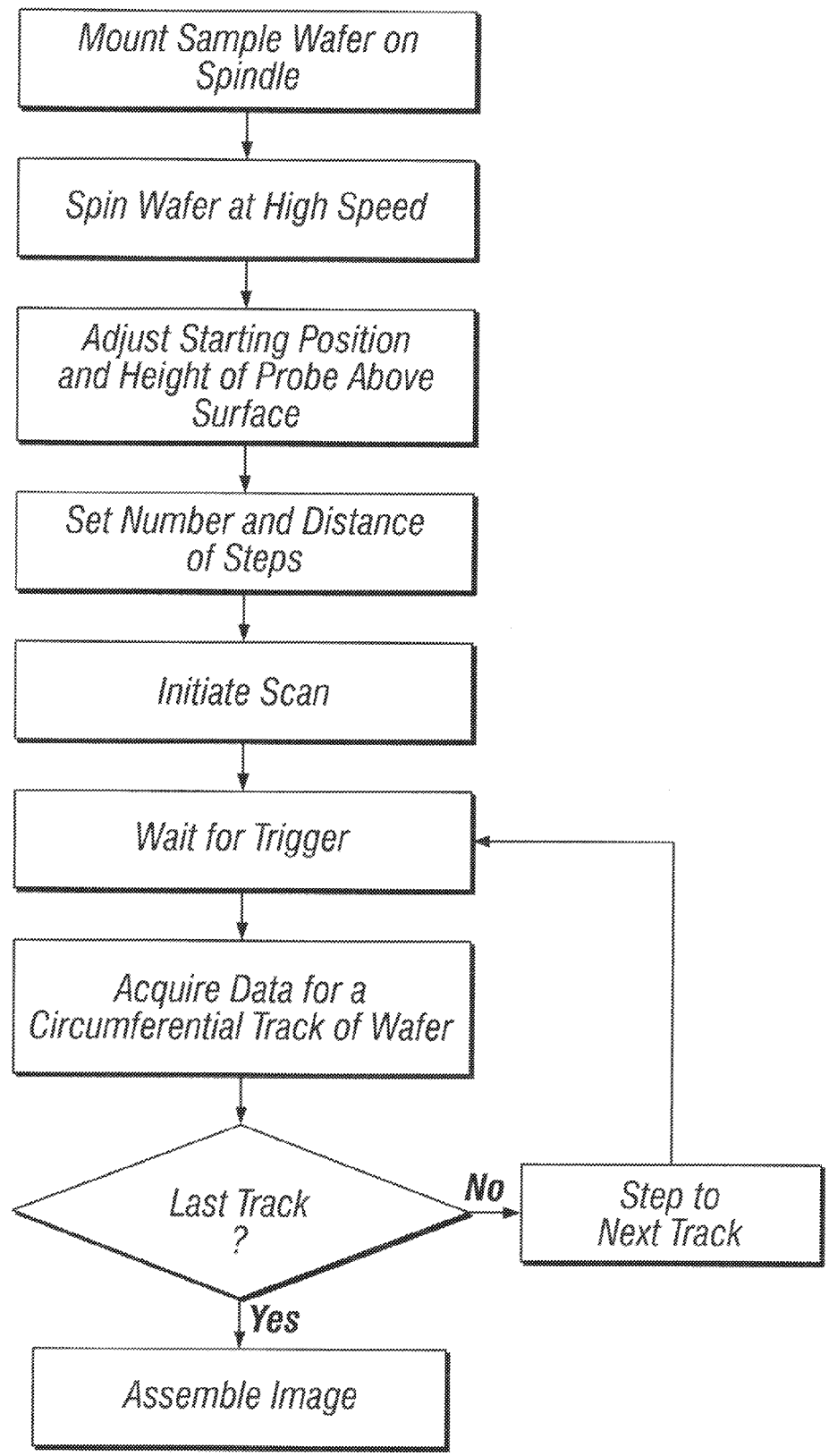
FIG. 9 illustrates a flow diagram for the image acquisition process of a radially scanned nvCPD imaging system.

The images generated by the scanning procedure of FIG. 9 were subsequently processed to automatically locate defects; thus locating areas of high variability. An ideal surface would exhibit a flat signal, but a wafer surface with defects would exhibit some variability in the signal. To locate areas with defects, the data was broken up into small areas of known location. The standard deviation of the signal within these areas was determined. Areas with defects showed a higher standard deviation, and these results can be seen in FIG. 6. Areas with defects appear brighter than lower variability areas of the wafer 15. This is one of many possible methods in accordance with the principles of the present invention to process the sensor data.

More generally, a defect can be identified by one or more of the following methods:—Process the data to look for a voltage or change in voltage (or pattern of voltages or changes in voltages) that exceeds some user—defined value (threshold).

Compare the data to a known pattern that represents a defect via some form of correlation or template matching.

Convert the spatial data to the frequency domain and then identify peaks in the frequency domain that represent defects with unique spatial characteristics.

These techniques can also be combined with other techniques to yield analytical results. The signal may also be preprocessed to facilitate defect detection, such as, for example:

Since the signal is differential, it can be integrated over some distance to produce voltages that represent relative CPD's over the surface of the wafer 15.

If the wafer 15 is "patterned", then this known pattern can be removed from the data prior to processing. This would likely be accomplished through some conventional method of variation of image or signal subtraction in either the space or frequency domains.

The signal would likely be processed with some form of frequency filtering to remove high or low frequencies depending on the size, shape and other characteristics of the expected defects.

The signal could be processed to remove features of a certain size by doing what is called "morphological processing" which is by itself well known in other applications.

Figure 22A:
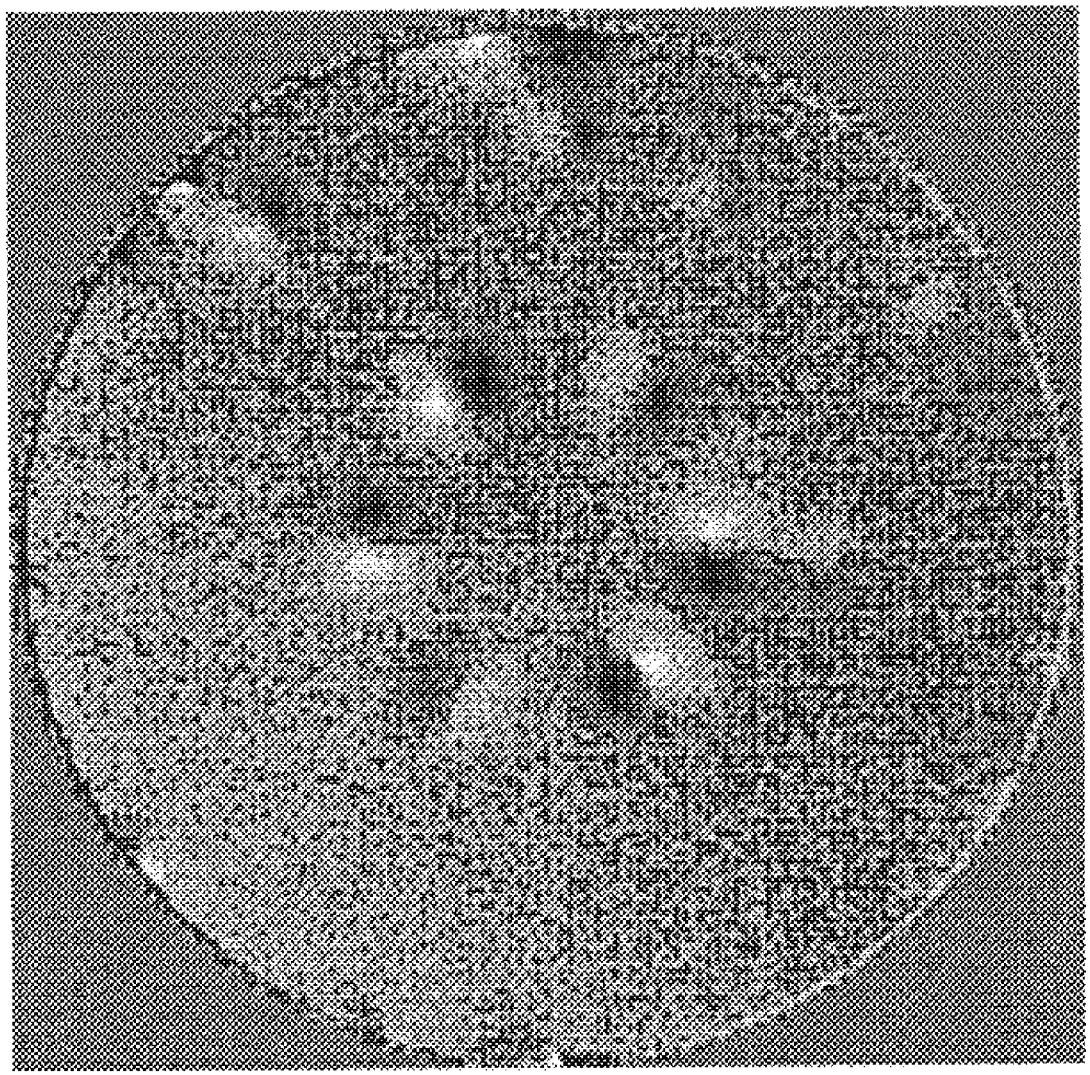
FIG. 22A is a 2D Edge Detection optical view using Canny Algorithm at Multiple Resolutions (#7 Wafer dipped into a CMP Slurry)
Figure 22B:
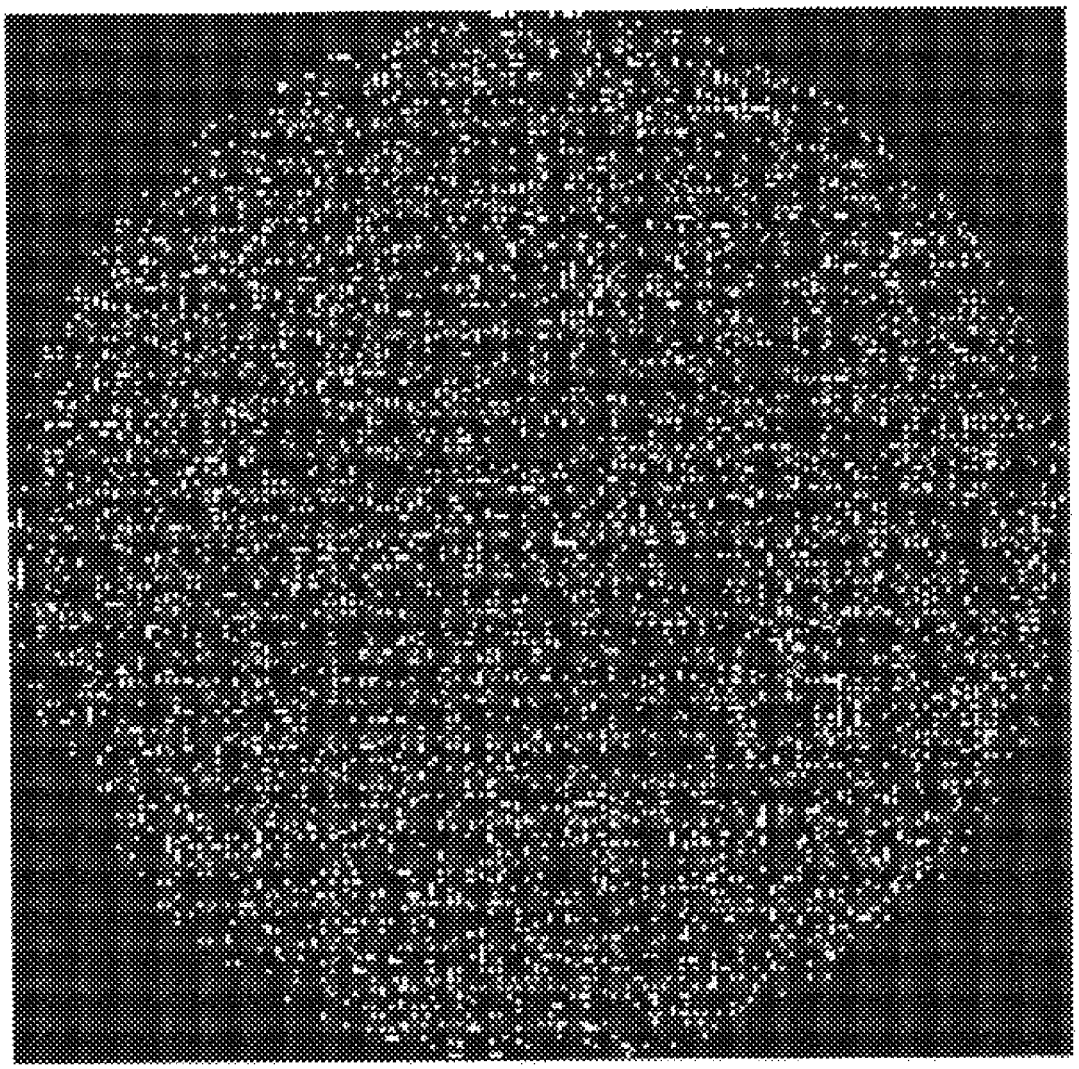
FIG. 22B is a 2D Edge Detection image produced in accordance with the principles of the present invention using Canny Algorithm at Multiple Resolutions (#7 Wafer dipped into a CMP Slurry, threshold=0.00001, Contamination Level=24.5)
Figure 22C:
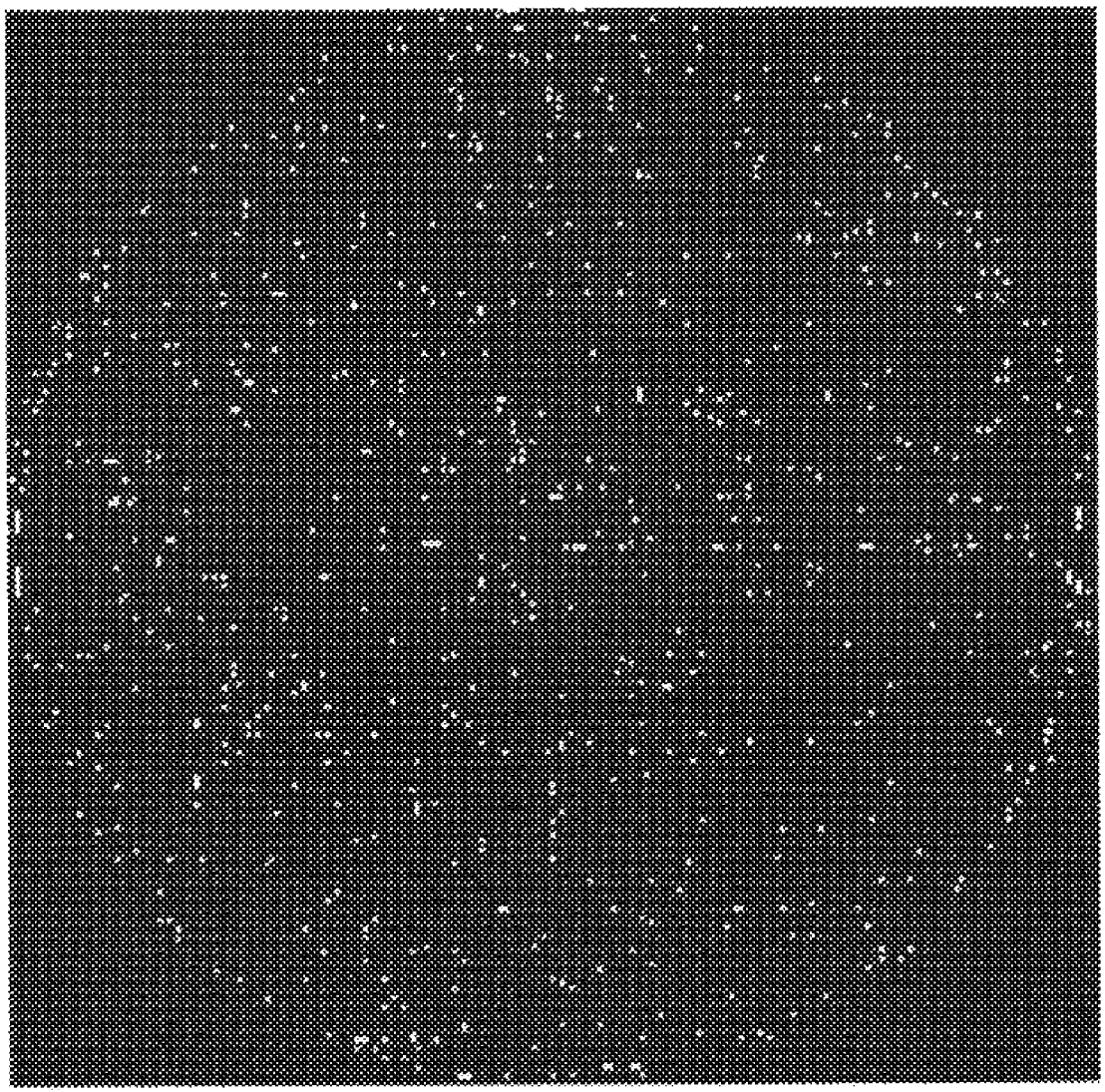
FIG. 22C is a 2D Edge Detection image produced in accordance with the principles of the present invention using Canny Algorithm at Multiple Resolutions (#7 Wafer dipped into a CMP Slurry, threshold=0.008, Contamination Level=4.5)
Figure 22D:
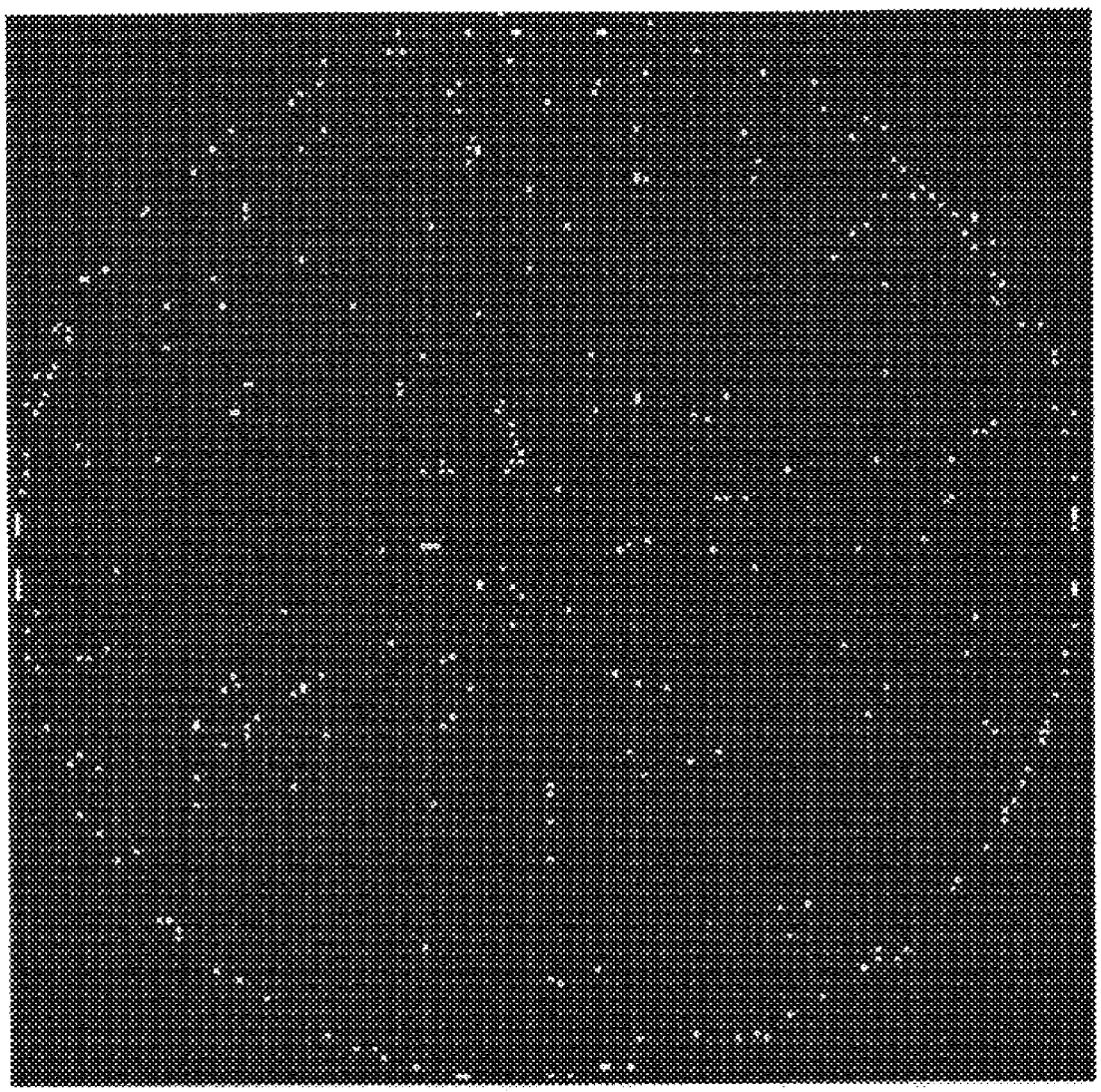
FIG. 22D is a 2D Edge Detection image produced in accordance with the principles of the present invention using Canny Algorithm at Multiple Resolutions (#7 Wafer dipped into a CMP Slurry, threshold=0.01, Contamination Level=1.9)
Figure 22E:
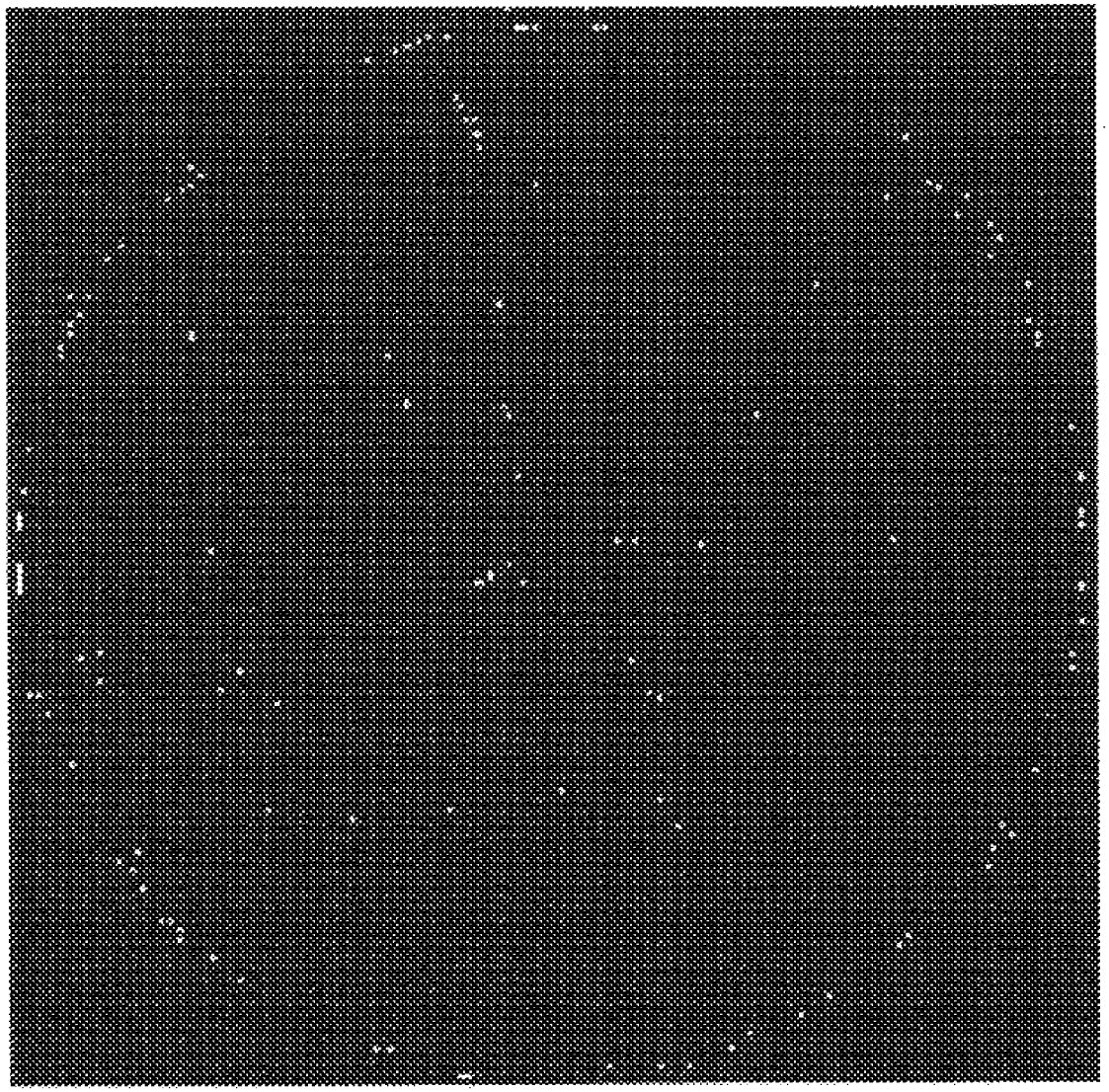
FIG. 22E is a 2D Edge Detection image produced in accordance with the principles of the present invention using Canny Algorithm at Multiple Resolutions (#7 Wafer dipped into a CMP Slurry, threshold=0.012, Contamination Level=1.1)
Figure 22F:
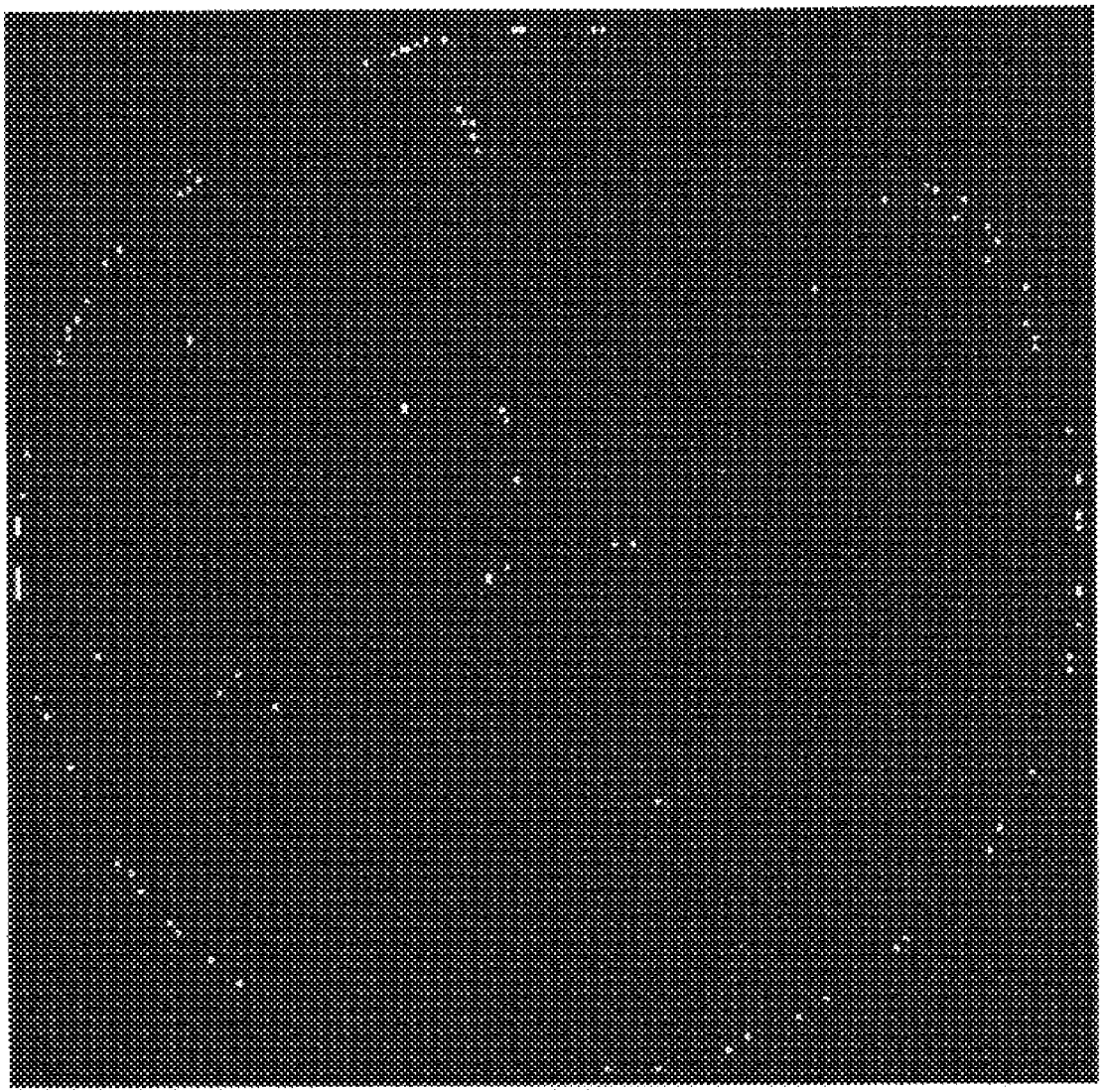
FIG. 22F is a 2D Edge Detection image produced in accordance with the principles of the present invention using Canny Algorithm at Multiple Resolutions (#7 Wafer dipped into a CMP Slurry, threshold=0.014, Contamination Level=0.8)
Figure 23A:
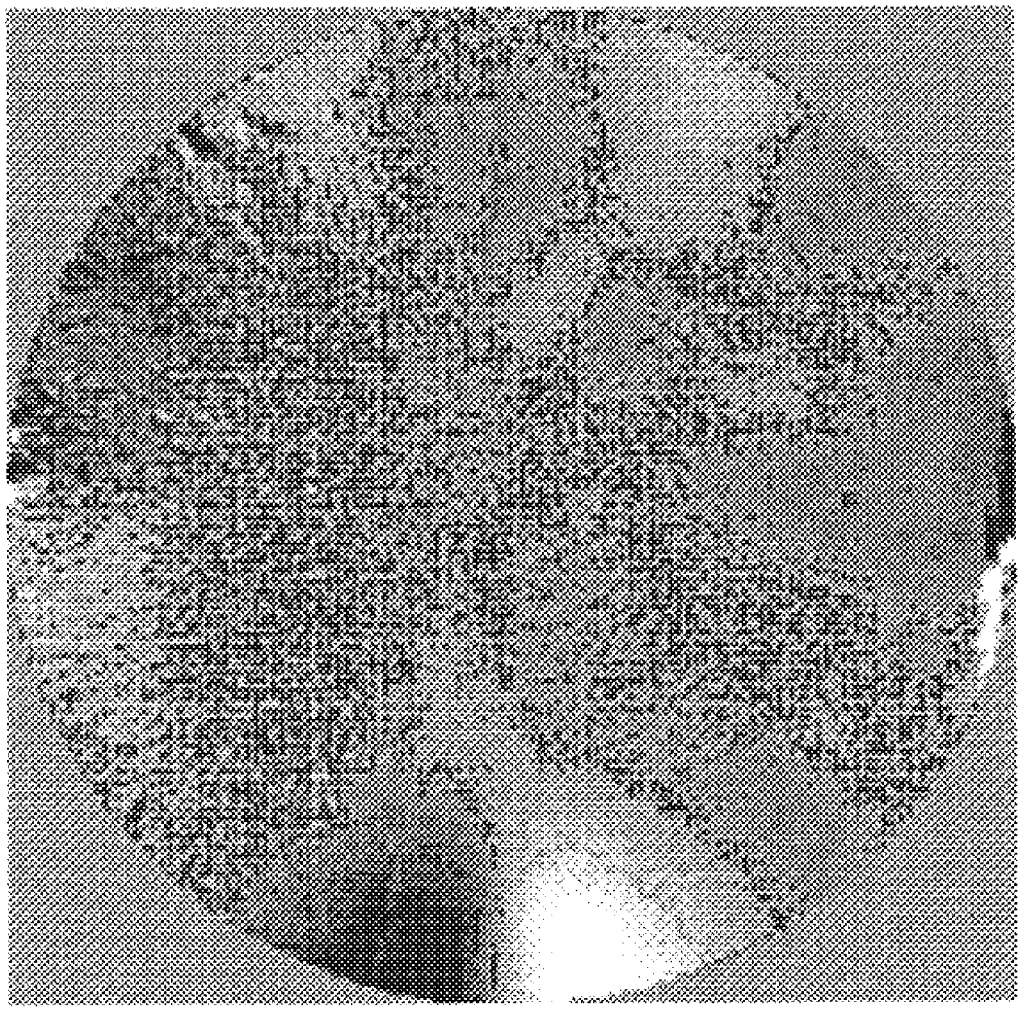
FIG. 23A an optical image of 2D Edge Detection produced in accordance with the principles of the present invention using Canny Algorithm at Different Scales (Qcept #6 Wafer dipped into a CMP Slurry)
Figure 23B:
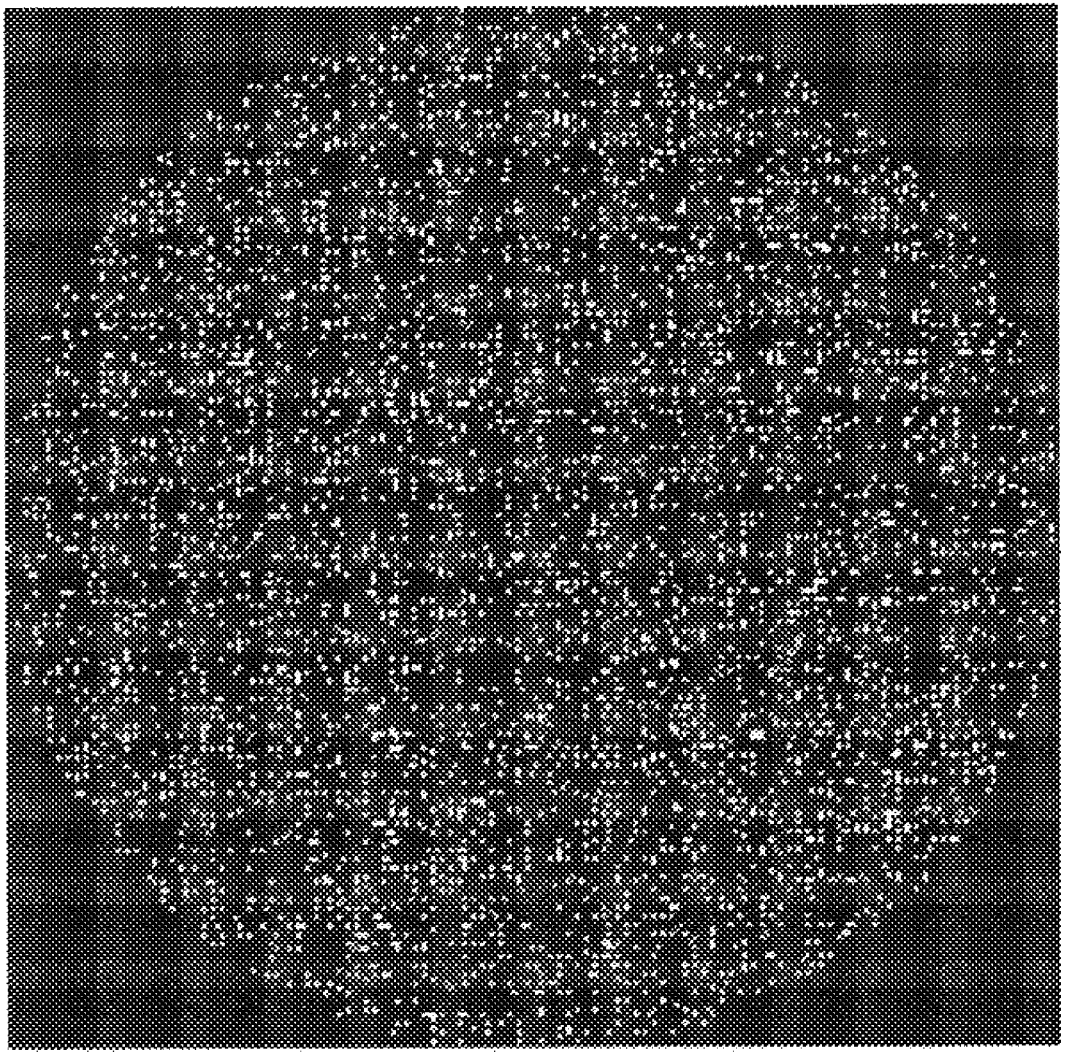
FIG. 23B an optical image of 2D Edge Detection produced in accordance with the principles of the present invention using Canny Algorithm at Different Scales (Qcept #6 Wafer dipped into a CMP Slurry, threshold=0.00001, Contamination Level=24.3)
Figure 23C:
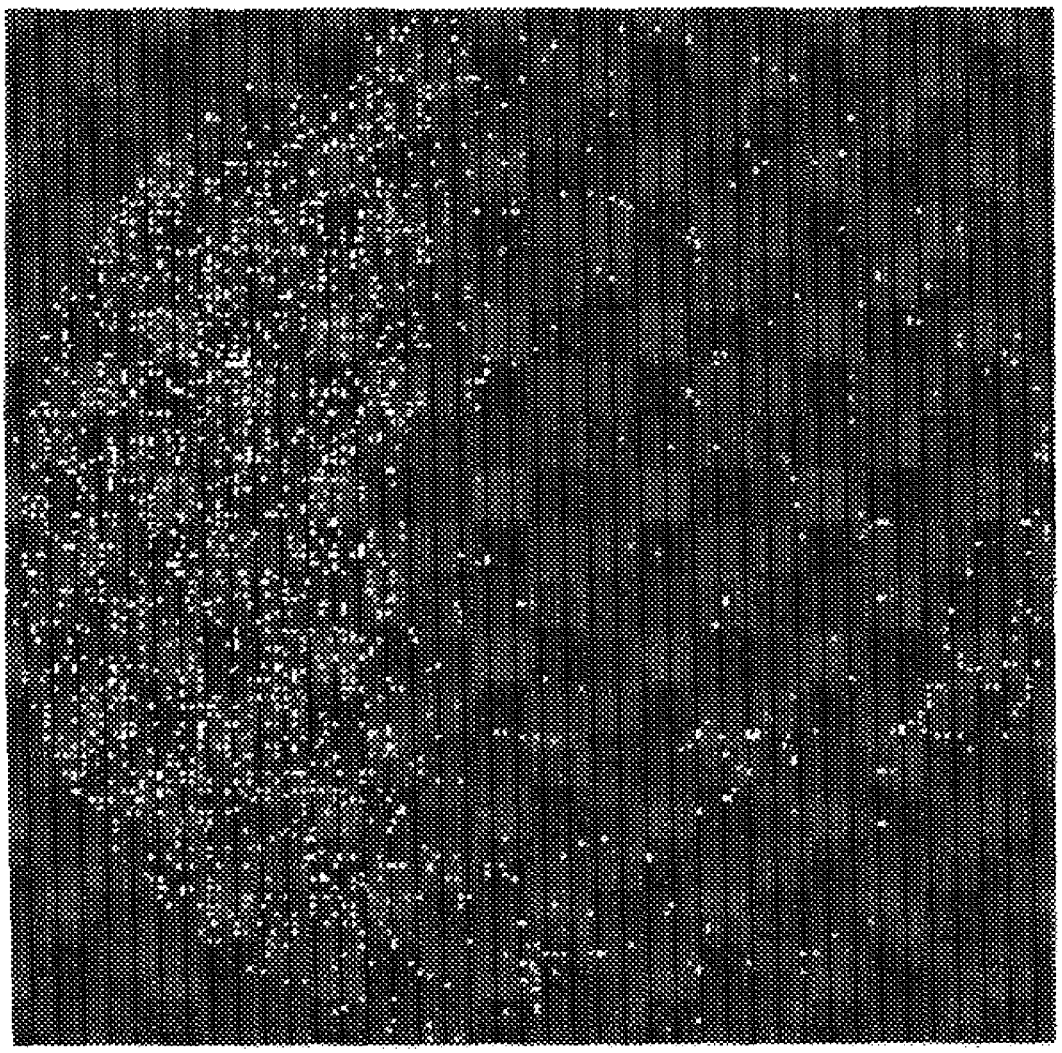
FIG. 23C an optical image of 2D Edge Detection produced in accordance with the principles of the present invention using Canny Algorithm at Different Scales (Qcept #6 Wafer dipped into a CMP Slurry, threshold=0.005, Contamination Level=9.6)
Figure 23D:
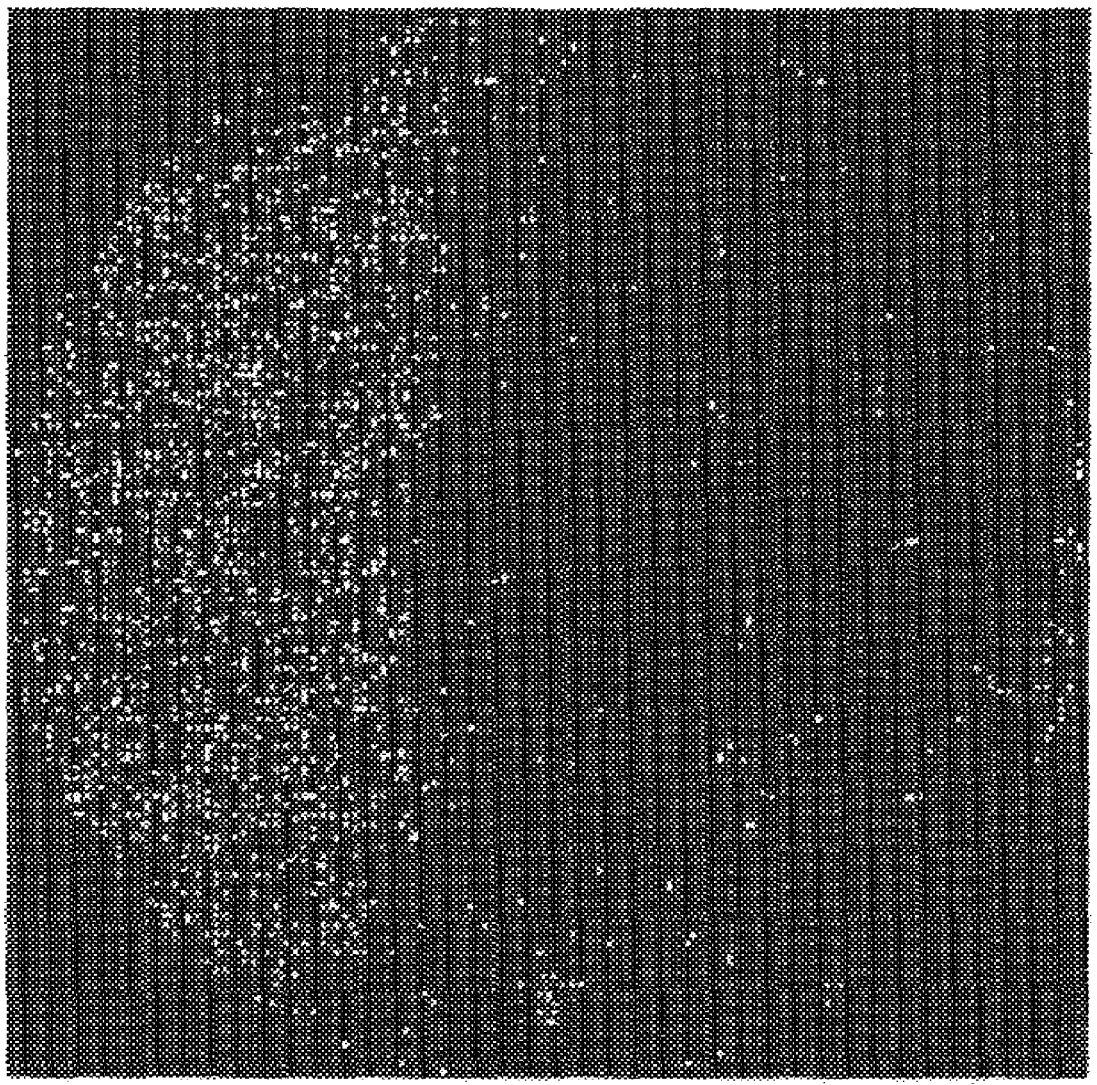
FIG. 23D an optical image of 2D Edge Detection produced in accordance with the principles of the present invention using Canny Algorithm at Different Scales (Qcept #6 Wafer dipped into a CMP Slurry, threshold=0.006, Contamination Level=8.2)
Figure 23E:
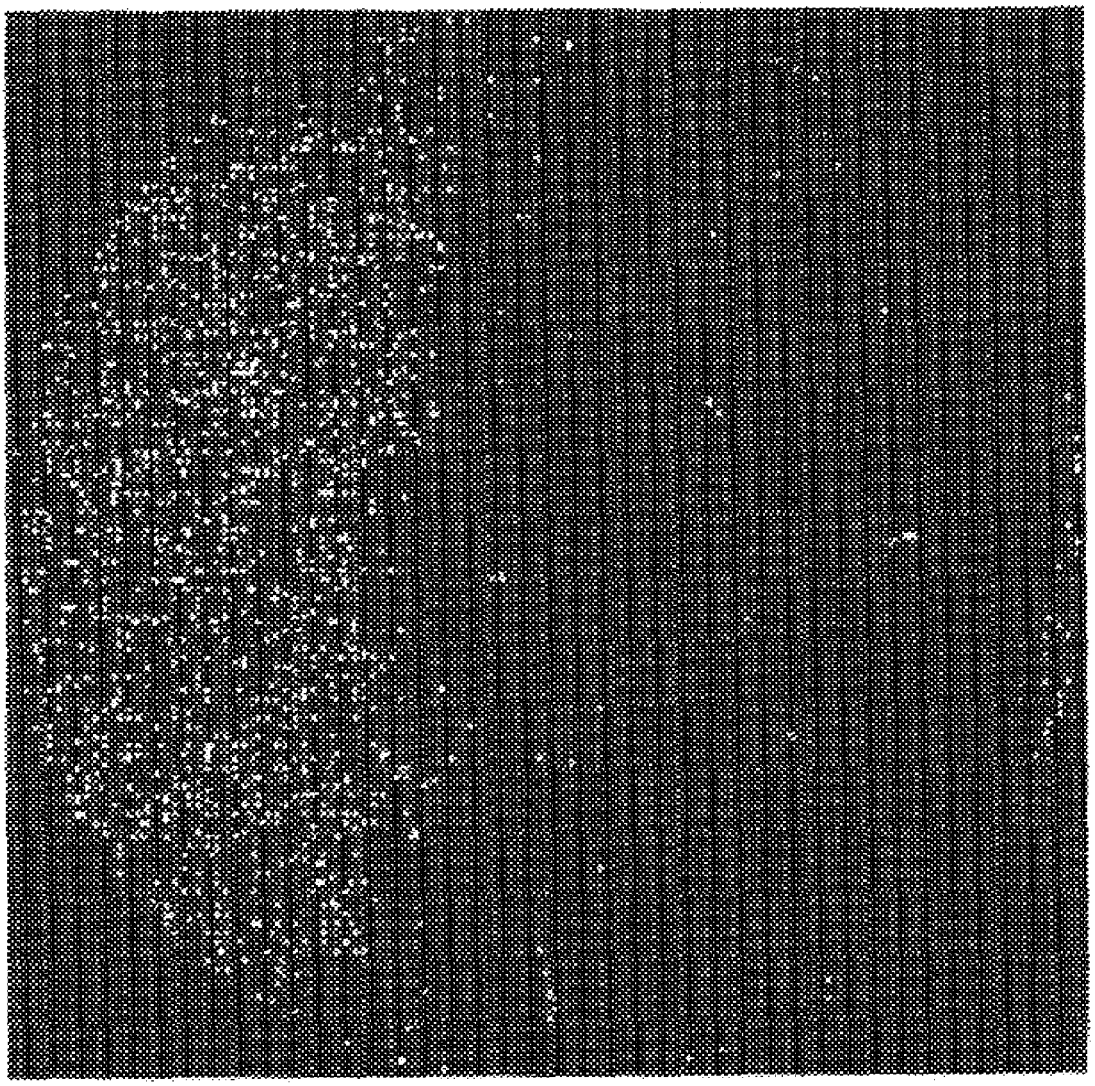
FIG. 23E an optical image of 2D Edge Detection produced in accordance with the principles of the present invention using Canny Algorithm at Different Scales (Qcept #6 Wafer dipped into a CMP Slurry, threshold=0.008, Contamination Level=6.9)
Figure 23F:
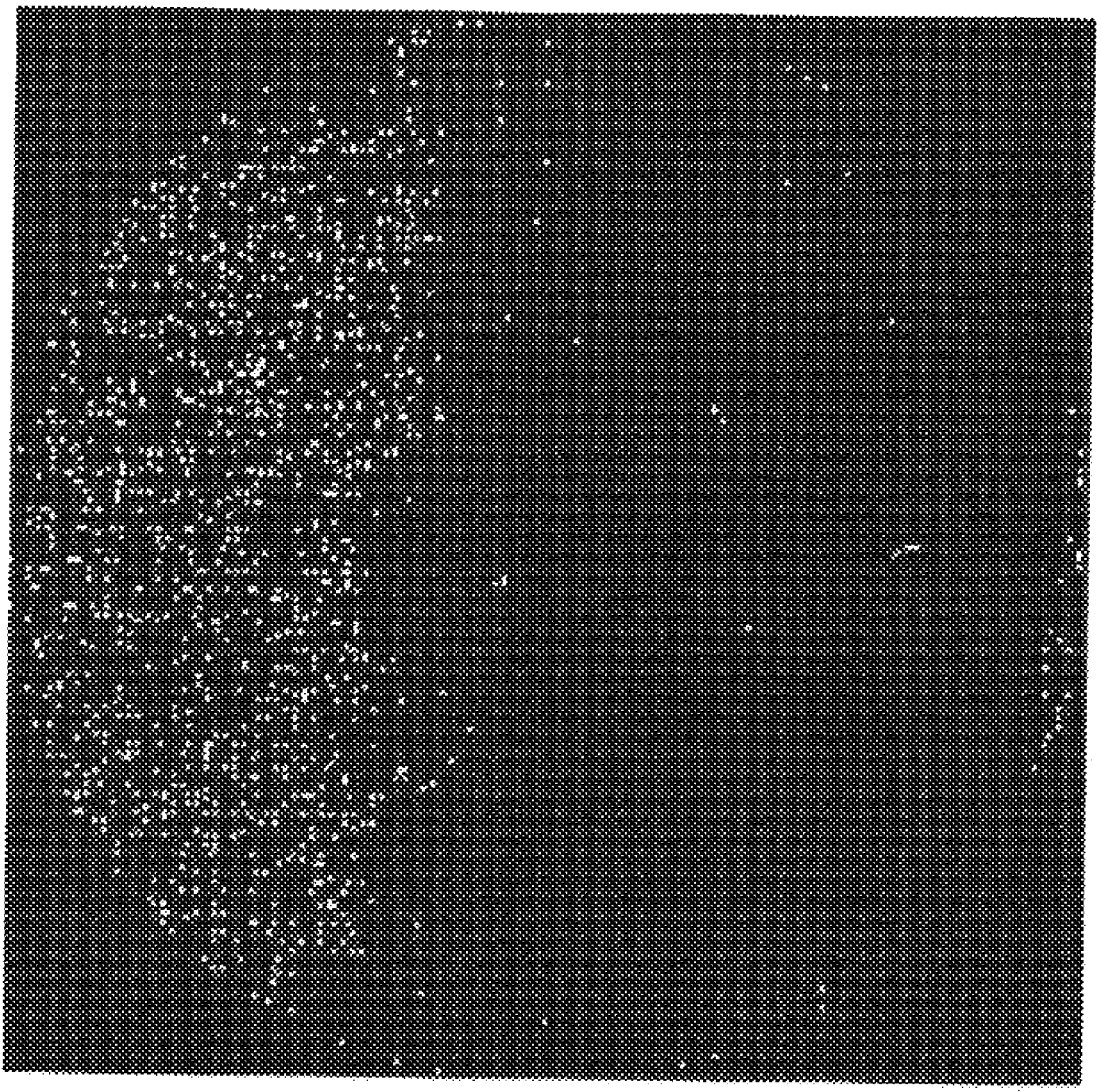
FIG. 23F an optical image of 2D Edge Detection produced in accordance with the principles of the present invention using Canny Algorithm at Different Scales (Qcept #6 Wafer dipped into a CMP Slurry, threshold=0.009, Contamination Level=6.4)

In one embodiment, a defect is detected and the contamination level is quantified based on an edge detection algorithm, such as but not limited to a Canny Edge detection algorithm. Multiple resolutions may be used or multiple scales or a combination thereof. FIGS. 22B–F depict the edge detection at various resolutions and is shown in comparison to an optical image (FIG. 22A). FIGS. 23B–F depict edge detection at various scales and in comparison to an optical image (FIG. 23A). In a preferred example of such an embodiment, the contamination is detected and quantified using the steps of:

Generating a CPD sensor peak signal at the boundary between two different areas (The peak signals behave much like the "edges", an image processing term. So, the contaminated area can be located by edge detection.);

Apply an Edge detection algorithm (such as the 2D Canny algorithm);—Multiple resolutions with different thresholds (thereby enabling detection of various size of contaminants, i.e. the higher resolution (lower threshold) will find the smaller contaminants);

Quantifying contamination level (CL) by the edge area over the total wafer area in the simplest way.

As previously discussed, determining a reference point for the sensor is necessary for optimal results. In one embodiment, the reference point is at the center of rotation (in the X-Y plane) and at the height of the surface of the wafer (on the Z axis). To find this point, the center of rotation and the height of the surface of the wafer must be determined, and then the height sensor is correlated with the Z position of the nvCPD sensor.

To find the center of rotation, the nvCPD sensor and motion system are used to find a geometrical and/or chemical feature on the surface of the spinning wafer at three or more points. Since the wafer is spinning, the feature describes a circle. The center of the circle is the center of rotation. Given the coordinates of three distinct points ($A(x_1, y_1)$, $B(x_2, y_2)$, and $C(x,y)$) on the diameter of the defined circle on the circle, its center is found algebraically by the equation: $(x-x_1)(x-x_2)+(y-y_1)(y-y_2)=0$.

Due to slight measurement errors, a different set of points might yield slightly different center coordinates. The "true" center of rotation is deemed to be the locus (average) of these points.

In one embodiment, to find the height of the surface of the wafer without touching the wafer surface, two sensors, the nvCPD sensor and a height sensor (which could itself be an nvCPD sensor in an embodiment discussed below) can be used. The nvCPD sensor and height sensor are calibrated so that when a reading is taken with the height sensor, the Z-axis coordinate of the tip of the nvCPD sensor is ascertained. (This calibration procedure is described below.) At that point, the readings of the height sensor are correlated with the Z position of the nvCPD sensor. Thereafter, the height sensor is used to detect the position of the surface of the wafer without touching it, and then the tip of the nvCPD sensor positioned accordingly.

In one embodiment, the height sensor is correlated with the Z position of the nvCPD sensor based on two assumptions: first, that within its usable range, measurements from the height sensor are linear in the Z axis and that a constant, k, can map changes in height measurements to proportional changes in Z; and second, that the relative positions of the height sensor and nvCPD sensor are fixed, i.e. the two sensors can move relative to the rest of the world but only as a unit; they, therefore, cannot move independently. Based on these assumptions, a point, P, is picked in the X-Y plane where calibration is to be performed. The height sensor is positioned above P, and a measurement from the height sensor, Hm, correlated with a coordinate on the Z axis, $Z_h$. Next the nvCPD sensor is positioned above P and move it down until it touches at a point, $Z_c$. The nvCPD signal changes significantly when the sensor tip touches the surface. Once these values are known, the Z value of the point where the tip of the nvCPD sensor would touch the surface is derived with the following equation:

$$Z_{surface} = Z_{current} + Z_c - Z_h + (H_m - H_{current})/k$$

wherein:

$Z_{surface}$ is the height of the surface where the tip of the nvCPD sensor would touch $Z_{current}$ is the current height of the sensor $H_{current}$ is the current height sensor measurement As previously mentioned, the height of the sensor should be measured and controlled to produce repeatable results. It is also possible to use an nvCPD sensor to control the height in a semiconductor wafer inspection system in accordance with the principles of the present invention. In order to use the nvCPD sensor to control height, the system must provide the capability to apply a time-varying bias voltage between the probe tip and the wafer surface. As the bias voltage varies, it produces an output signal that is a function of the capacitance between the probe tip and the wafer surface. The closer the probe tip is to the surface, the larger the output voltage. After the relationship between height and capacitance is determined, the magnitude of the output signal can be used to calculate the height of the sensor. The signal magnitude can be calculated as the peak-to-peak, standard deviation, RMS, or some other measure known in the art.

Again, the formula for the output of the nvCPD sensor is:

$$i = C\frac{\partial V}{\partial t} + V\frac{\partial C}{\partial t}$$

The voltage V is the contact potential difference between the probe tip and the wafer surface. If a bias voltage is applied, the formula then becomes:

$$i = C\frac{\partial (V + V_b)}{\partial t} + (V + V_b)\frac{\partial C}{\partial t}$$

where Vb is the bias voltage. If the nvCPD sensor is not moving relative to the surface of the wafer (or is moving relatively slowly), then the capacitance C and the contact potential difference voltage V are not changing, and the equation becomes:

$$i = C\frac{\partial V_b}{\partial t}$$

Since the bias voltage is a known fixed frequency and magnitude, the output current is a function of the capacitance (C). C is a combination of the capacitance between the probe tip and wafer surface, and any stray capacitances in the circuit. The capacitance vs. height function can be characterized and used to determine the height of the nvCPD probe at a point above the wafer surface. Once the height of the sensor is determined, then the bias voltage can be turned off in order to make scanning nvCPD measurements.

Figure 18:
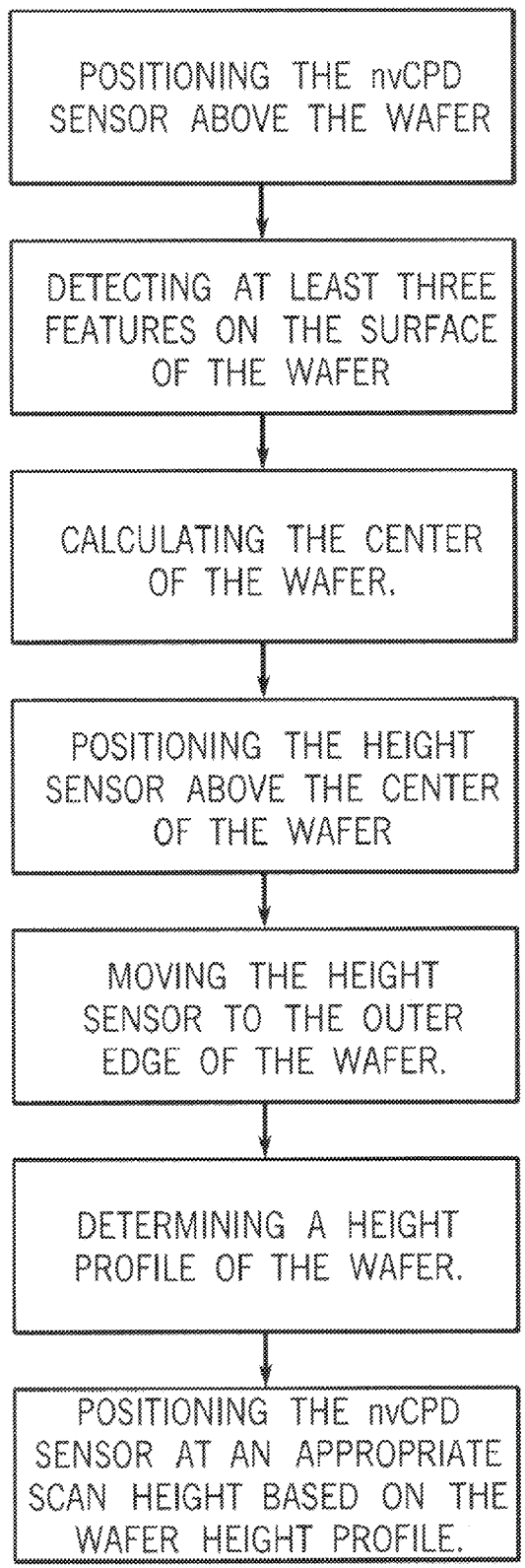
FIG. 18 is a detailed view of the Adjust Starting Position and Height of Probe Above Surface step of FIG. 9.

However, in some embodiments prior to scanning a portion of the wafer, a height profile is established with a height sensor and then the scanning height of the nvCPD sensor adjusted appropriately. FIG. 18 depicts one embodiment which utilizes a height profile of the wafer to position the sensor. The height profile is determined by first moving the height sensor to the center of rotation and then, with the wafer spinning, the height sensor is moved out toward the edge of the wafer until it senses the edge. Note that this also allows the diameter of the wafer to be determined. The sensor is then moved back toward the center until it is within the wafer flat(s) or notch. One or more height measurements taken along the way establish the profile. An appropriate height for nvCPD sensor scanning is calculated based on the profile, particularly based on the maximum detected height.

As mentioned above, often the nvCPD sensor used in accordance with the principles of the present invention generate a peak signal that behaves like noise. In accordance with the principles of the present invention, denoising algorithms can be applied to both nvCPD signals and nvCPD images. In one embodiment, the nvCPD signal/image data are decomposed into the wavelet domain using one of the wavelets available such as but not limited to 'Coiflet', 'Daubechies', 'Symmlet', and other such wavelets. Then, as a result of the wavelet decomposition, a series of wavelet coefficients are obtained at a finite number of scales that can be given by the user. A coefficient at a particular scale represents the magnitude of the frequency corresponding to that scale at the point corresponding to that coefficient. The nvCPD signal/image can then be reconstructed by the coefficients in reverse order.

Figure 19:
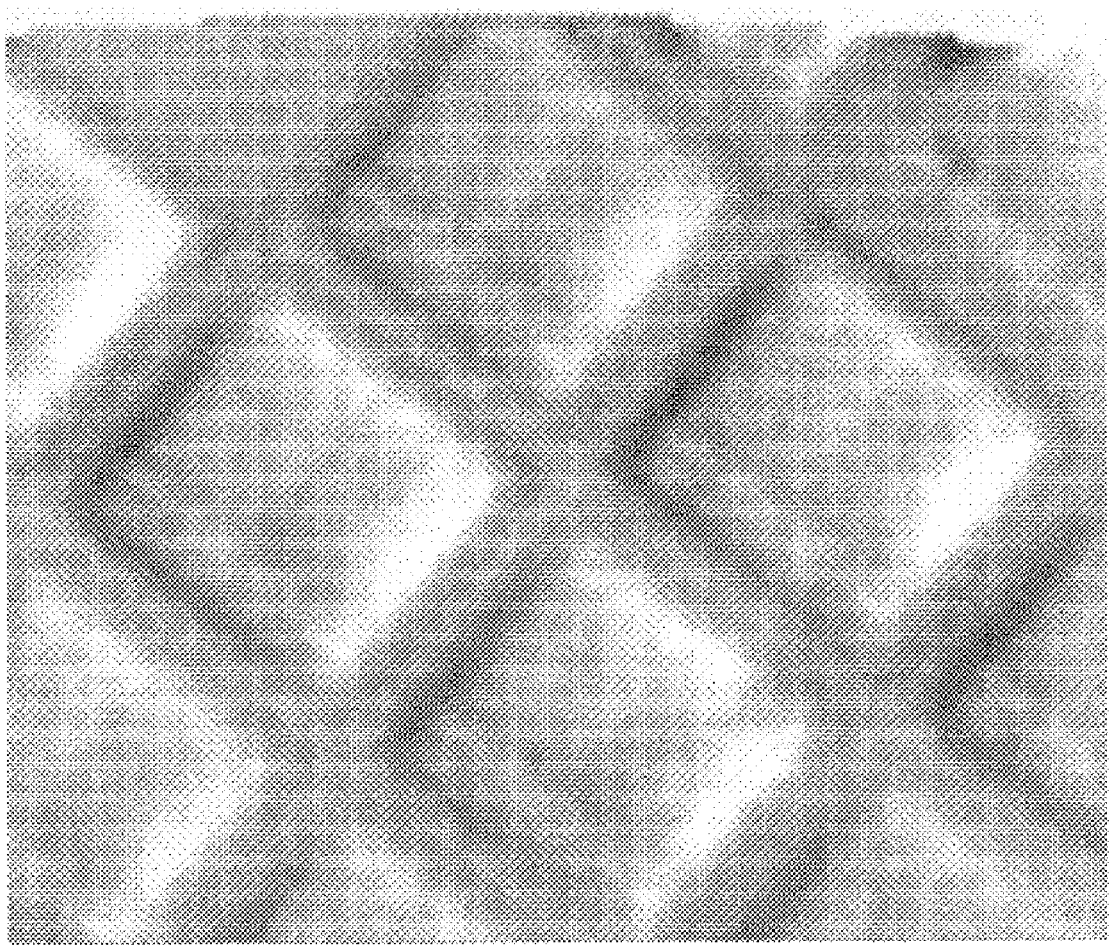
FIG. 19 illustrates NCVPD processed wafer images before deconvolution.
Figure 20:
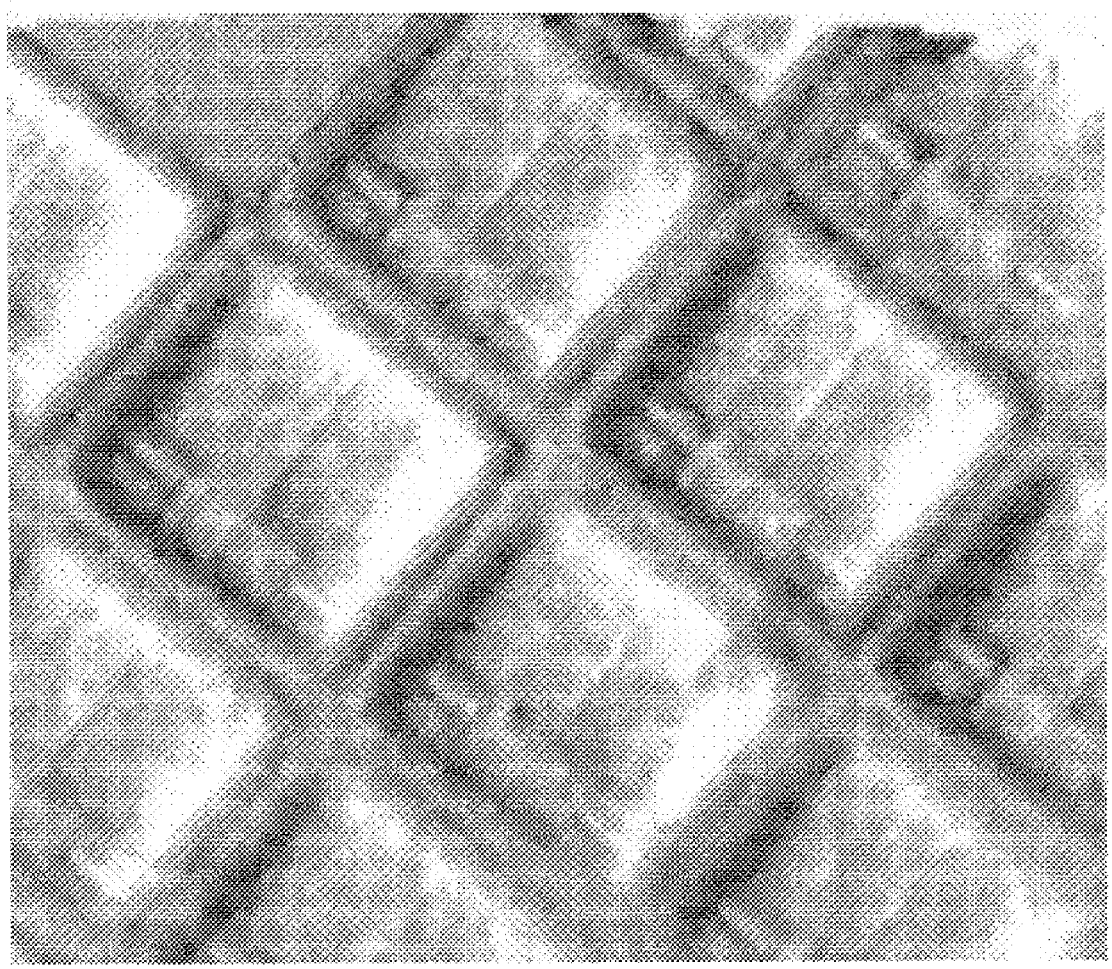
FIG. 20 illustrates NCVPD processed wafer images after deconvolution.

By adjusting the coefficients and performing reconstruction, the three components (peak, low frequency, and noise) of the nvCPD signal/image can be selectively filtered out. To eject the low frequency component from the nvCPD signal/image, only wavelet coefficients at fine scales are used for reconstruction since the low frequency component of the nvCPD signal/image are represented by the coefficients at coarse scales. To eject the noise from the nvCPD signal/image, the coefficients at fine scales can be shrunk softly based on the threshold given. The threshold can be determined using any one of numerous methods known in the art such as, but not limited to, 'Visu', 'SURE', 'Hybrid', 'MinMax'. The sharp peak signal that is related to contamination on the wafer can be reconstructed substantially in isolation by the wavelet coefficients resulting after the two processes above. Thus, noise such as vibrations or a wobbling of the wafer can be filtered out of the signal. FIG. 19 depicts an image produced by a system in accordance with the principles of the present invention without deconvoluting or denoising the data. FIG. 20 illustrates the improved resolution and definition of an image which is denoised in accordance with the principles of the preferred embodiment.

A semiconductor wafer inspection system in accordance with the principles of the present invention which utilizes a nvCPD sensor may, as discussed above, experience a time delay. However, the present invention provides a filtering technique to remove this time delay. First, the time delay circuit is modeled as a first order RC circuit. The continuous-time transfer function of the RC circuit is given by $$\frac{Y(s)}{X(s)} = \frac{1}{\gamma s + 1}$$

where X(s) and Y(s) are the Laplace transformation of the input current signal at the probe tip and the output voltage measurement to the data acquisition, and T is the time delay constant.

The continuous current signal is fed into and amplified by the amplifier, and then converted into a discrete signal through the A/D converter. In this way, the collected data by the computer at the final stage is a series of discrete data. For digital signal processing, the continuous-time transfer function of the RC circuit is converted into a discrete-time transfer function based on Z-transformation.

This discretized transfer function has the form $$\frac{Y(z)}{X(z)} = \frac{\alpha}{z + \beta}$$

wherein the constants $\alpha$ and $\beta$ are determined by the discretization method employed, the sampling time and the time delay constant, T.

Next, in a preferred embodiment, the impulse response of the discretized transfer function is determined. In general, the impulse response is a finite number of positive discrete values that converges to zero gradually. Once the impulse response is found, the deconvolution process with the impulse response is performed on each track data separately.

Figure 16:
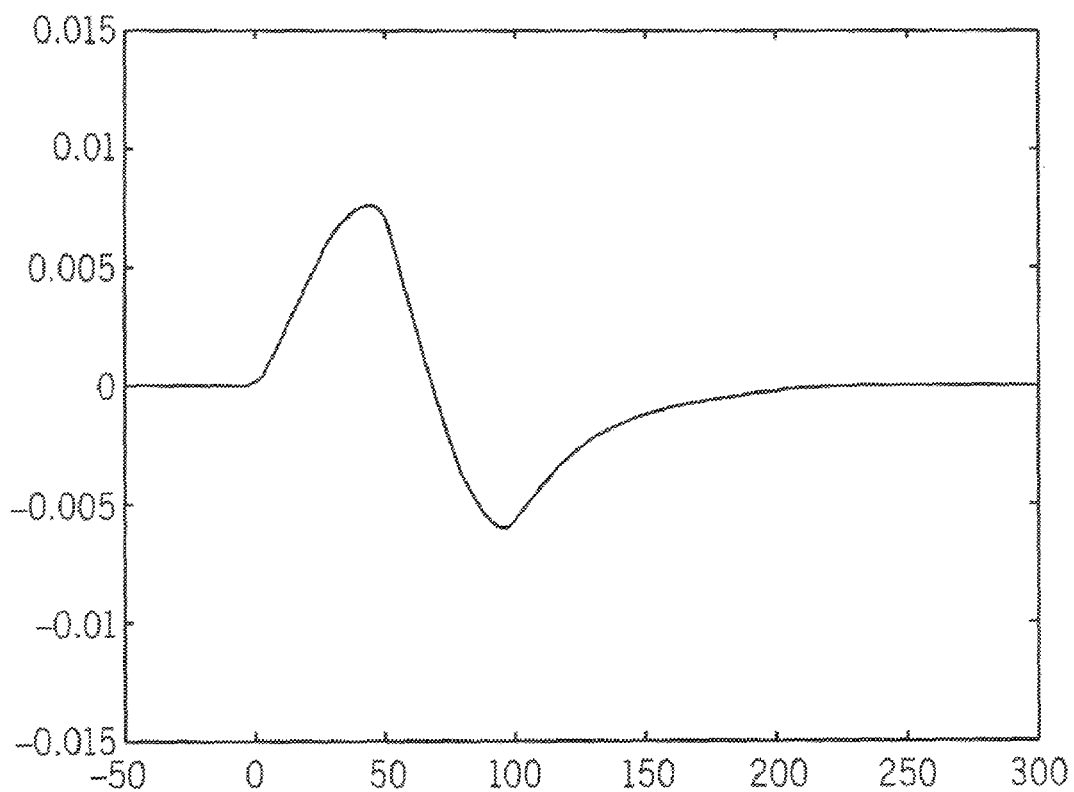
FIG. 16 illustrates a chart depicting a typical nvCPD signal where there is a set of peaks comprising a positive peak and a negative peak having non-equivalent heights.
Figure 17:
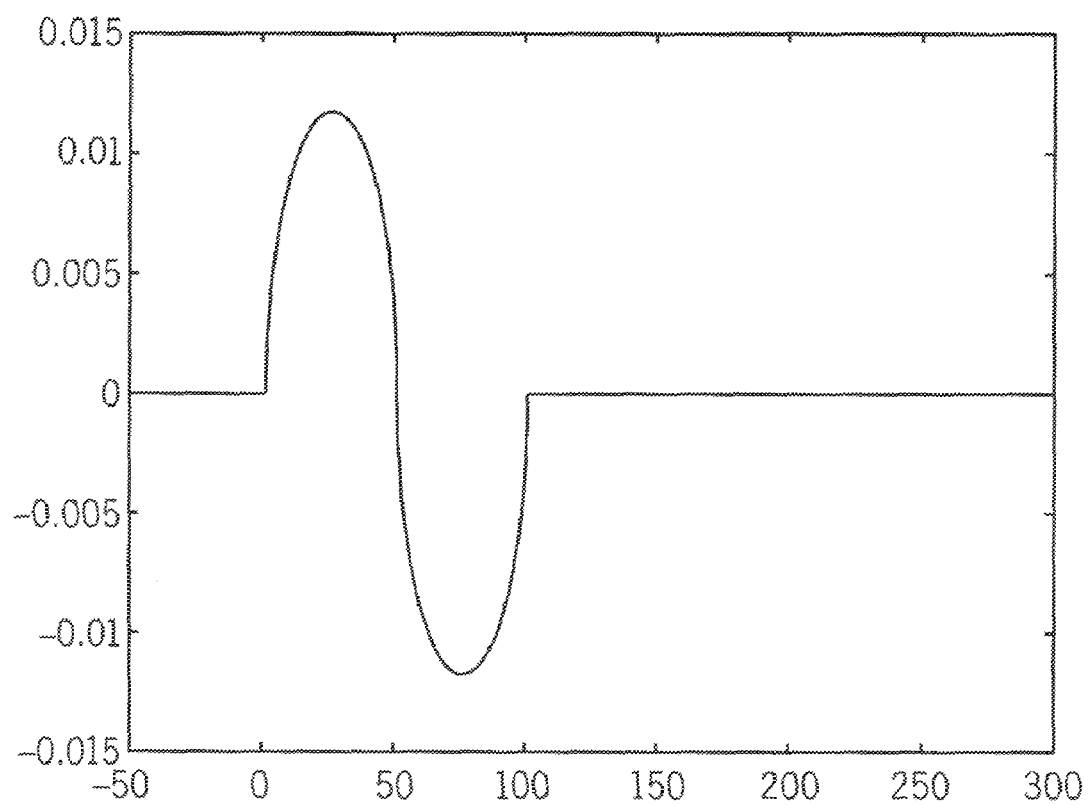
FIG. 17 illustrates a chart depicting a signal output of one embodiment of the present invention where the positive peak height is substantially equivalent to the negative peak height.

Time constant prediction is important and can be assessed by comparing the positive peak height and the negative peak height. FIG. 16 shows a typical nvCPD signal where there is a pair of a positive peak and a negative peak. It is shown that the positive peak is higher than the negative peak. With zero time delay, the signal would look like FIG. 17, where the positive peak height is equivalent to the negative peak height.

By comparing the positive peak height with negative peak height, the time constant can be estimated correctly. If the time constant is underestimated, the former peak (in this example, the positive peak) is higher than the latter peak (in this example, the negative peak). If the time constant is overestimated, the former peak is lower than the latter peak. By varying the time constant, a point when the positive and negative peaks are equivalent in height could be found to predict the time constant correctly.

Figure 24:
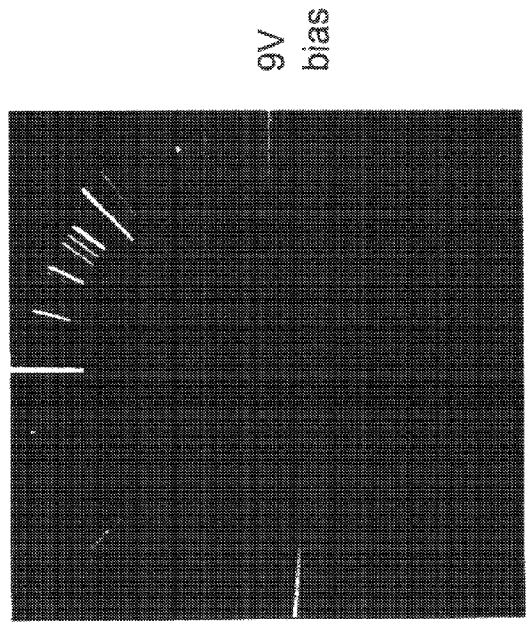
FIG. 24A shows an image of a semiconductor wafer generated by an apparatus of the present invention with no bias voltage.
FIG. 24B shows the image of the same semiconductor wafer where a 9 volt bias is applied.
FIG. 24C shows the image generated by an apparatus of the present invention, where the bias signal has been eliminated as shown mathematically below.
FIG. 24D illustrates the composition of the semiconductor wafer inspected in FIGS. 24A–C.
Figure 24:
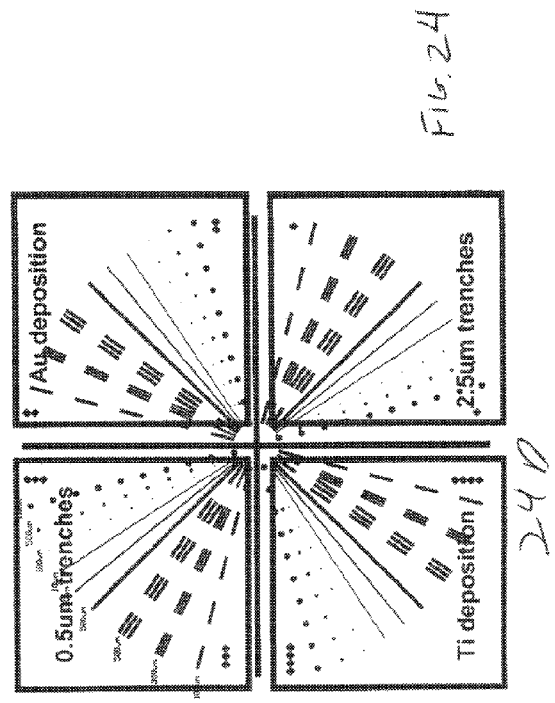
Figure 24:
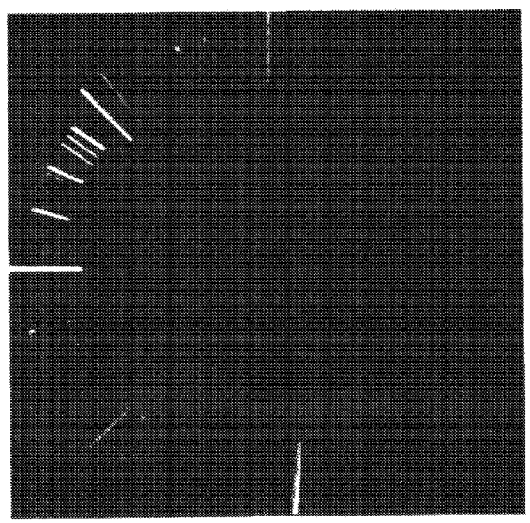
Figure 24:
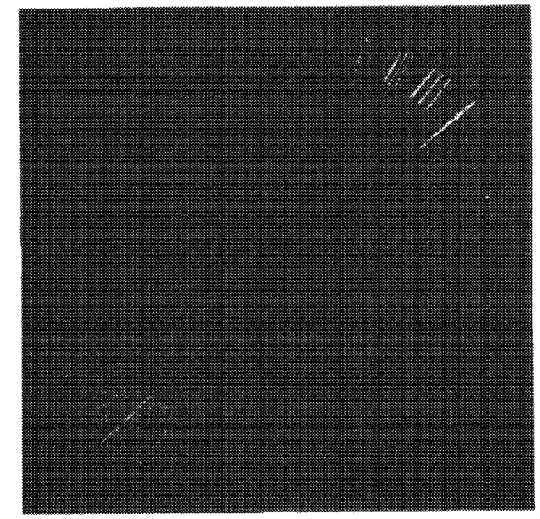

In one exemplary embodiment, the present invention provides a method and apparatus to allow for the isolation of the topographical information by filtering out the chemical information from the sensor apparatus. This embodiment utilizes a direct current (D.C.) bias applied to the system. In one exemplary embodiment, the bias is applied to the sensor. In another exemplary embodiment, a similar bias is applied to the sample surface directly instead of to the sensor. A first scan of the sample surface is taken with a negative bias applied to either the sample or the probe and the data is recorded. A second scan of the wafer is taken with a positive bias applied to which ever of the probe or the probe had the bias applied during the first scan. One of ordinary skill in the art will appreciate that this order could be reversed and the positive bias scan could be done first followed by a negative bias scan. The signal with the negative bias applied is then subtracted from the signal with the positive bias leaving a signal related only to geometric change on the sample surface. FIGS. 24A–D illustrate the images of a wafer at each of the various steps. FIG. 24A shows an image of a semiconductor wafer generated by an apparatus of the present invention with no bias voltage. FIG. 24B shows the image of the same semiconductor wafer where a 9 volt bias is applied. FIG. 24C shows the image generated by an apparatus of the present invention, where the bias signal has been eliminated as shown mathematically below. FIG. 24D illustrates the composition of the semiconductor wafer inspected in FIGS. 24A–C. As can be seen, the geometrical or topographical features were strengthened while the chemical features were weakened. The basic equations relating to nvCPD inspection can be used to illustrate this embodiment.

As previously stated, the basic CPD equation is:

$$i = C\frac{dV}{dt} + (\phi_P - \phi_S)\frac{dC}{dt}$$

The equation with positive bias applied is:

$$i_{+Bias} = C\frac{dV}{dt} + (\phi_P - \phi_S + V_{Bias})\frac{dC}{dt}$$

The equation with negative bias applied is:

$$i_{-Bias} = C\frac{dV}{dt} + (\phi_P - \phi_S - V_{Bias})\frac{dC}{dt}$$

Thus, by subtract the signal with a negative bias from the signal with a positive bias results in:

$$i^* = i_{+bias} - i_{-bias} = 2V_{Bias}\frac{dC}{dt}$$

Solving the difference shows the signal dependent on only geometry changes of surface (represented by capacitance)

$$i^* = 2V_{Bias}\frac{dC}{dt}$$

In an exemplary embodiment, the present invention relates to a method and apparatus to allow for the preservation of signal to noise ratio and for providing a substantially uniform data density by varying the rotational speed to provide substantially uniform linear speed of the sample relative to the probe. A variable speed chuck is provided which decreases the rotational velocity in proportion with the motion of the probe to provide the probe with substantially even data exposure. Thus, the chuck is able to compensate for the increasing data per revolution by reducing the revolutions per minute to maintain a substantially even data density.

In an exemplary embodiment, the system of the present invention includes a plurality of probes. The tips of each of the plurality or probes may be arranged in a variety of different arrangements known in the art, including but not limited to linear arrays and two-dimensional arrays. It has been shown that multiple probe tips in a variety of configurations, as just discussed, provide the system of the present invention with a decrease in the time required to scan a sample surface. The decrease in speed is inversely proportional to the percentage increase in the number of probes used. The individual probes in the plurality have, in one exemplary embodiment, varying characteristics. Such characteristics may include, but are not limited to, bias voltage and height. It is believed that the use of a plurality of probes provides, in addition to a decreased inspection time, an improvement in lateral resolution and chemical sensitivity. Such an improvement in lateral resolution and chemical sensitivity may be accomplished, in one embodiment, by the use of differentially comparing the separate probe data streams such as by a combination of separate voltage tracks.

In another exemplary embodiment, a method is provided for calibrating the height of the probe tip. This procedure assumes that the height sensor and nvCPD sensor are rigidly mounted with respect to each other, and that the relative height of the sensors (z) can be precisely determined. In our system, the height sensor and nvCPD sensor are mounted to the same metal fixture, and their relative height is determined by reading the z-axis encoder on the positioning system.

Figure 25:
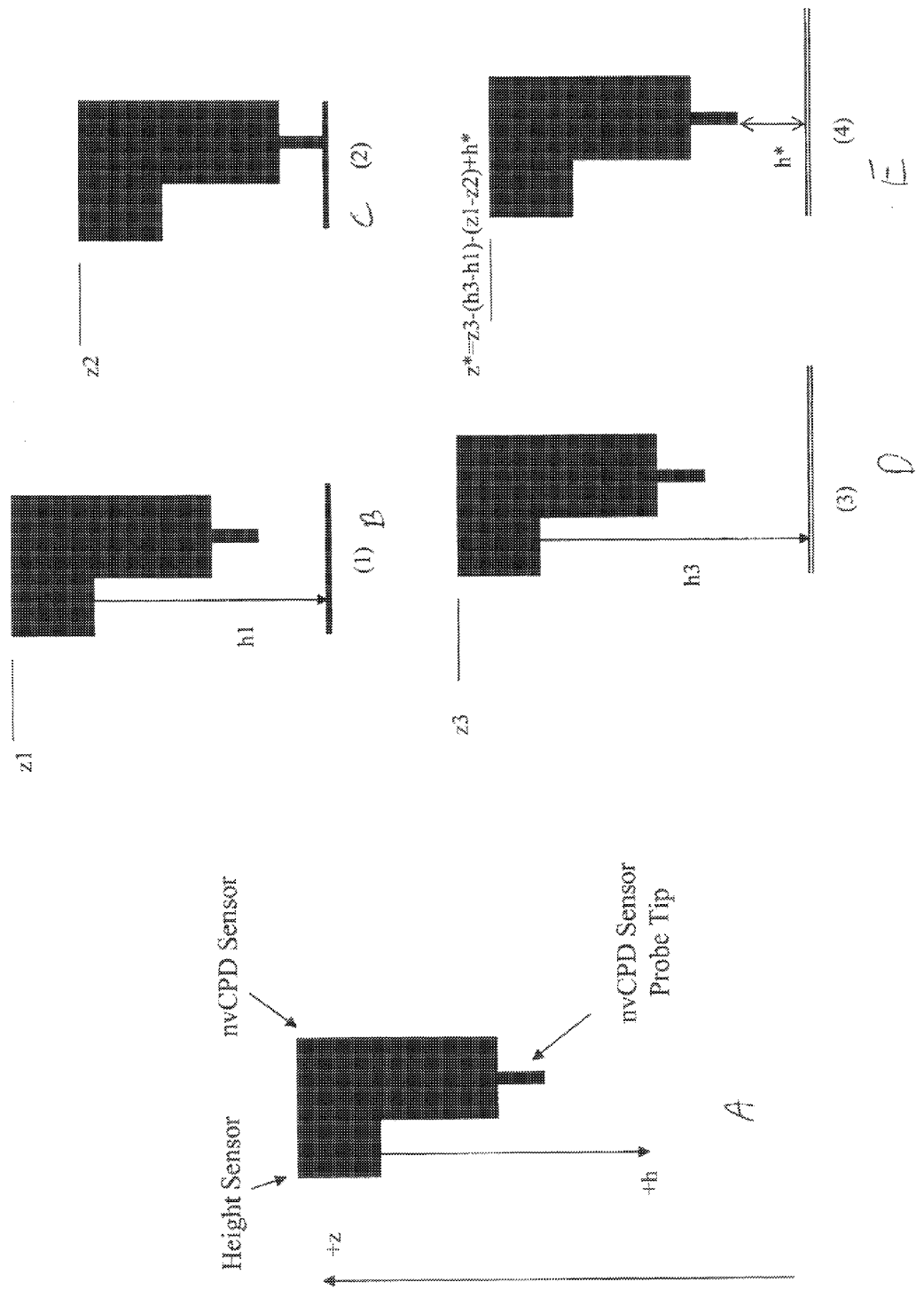
FIG. 25A illustrates an apparatus for calibration according a calibration process of the present invention for calibrating the height of the nvCPD sensor.
FIG. 25B shows the height sensor positioned above a reference surface so that the distance between the reference surface and the height sensor is within the range of detection for the height sensor.
FIG. 25C shows the nvCPD sensor moved slowly down while the level of the nvCPD signal is monitored.
FIG. 25D shows that if the desired height is h*, then the height sensor is positioned above the surface so that the surface is within the measurement range of the height sensor.
FIG. 25E illustrates that the nvCPD sensor is height adjusted to $z^*=z3-(h3-h1)-(z1-z2)+h^*$, which results in a height of the nvCPD sensor probe tip above the surface of h*.

In one exemplary embodiment illustrated in FIGS. 25A–E, the present invention includes a calibration process for calibrating the height of the nvCPD sensor. The calibration process is as follows. (1) As shown in FIG. 25B, the height sensor is positioned above a reference surface so that the distance between the reference surface and the height sensor is within the range of detection for the height sensor. The height of the sensors is recorded as z1. The height sensor reading is recorded as h1. As shown in FIG. 25C, the nvCPD sensor is moved slowly down while the level of the nvCPD signal is monitored. When the nvCPD sensor probe tip contacts the reference surface then the output of the nvCPD sensor experiences a significant change. This is automatically detected by the scanning system and the downward motion stops. The height is recorded as z2. The nvCPD sensor probe tip can now be positioned at a desired height above any surface. This is accomplished as follows. As shown in FIG. 25D, if the desired height is h*, then the height sensor is positioned above the surface so that the surface is within the measurement range of the height sensor. The height is recorded as z3 and the height sensor reading is recorded as h3. As shown in FIG. 25E, the nvCPD sensor is then positioned above the same point and the height adjusted to z*=z3−(h3−h1)−(z1−z2)+h*, which results in a height of the nvCPD sensor probe tip above the surface of h*.

Although the present invention has been frequently described in relation to the scanning of a semiconductor wafer which is spun relative to a probe which takes circumferential tracks of data, one skilled in the art would appreciate that the present invention is not limited to such. For example, the present invention may, in one exemplary embodiment, be used to scan liquid crystal display panels, which are generally to bulky to be spun. In this embodiment, the probes are raster-scanned across the sample surface. In addition, in another exemplary embodiment, the probe may be held stationary and the sample surface moved relative thereto. In yet another exemplary embodiment, the sample surface may be held stationary and the probe may be moved relative thereto.

The following non-limiting example describes methods of preparation of test wafers and sensing characteristic images for identifying certain defect states, chemical states, electrostatic states and mechanical features present on a semiconductor wafer surface.

EXAMPLE

Sample wafers can be created by dip coating the wafer 15 in solutions that contain known concentrations of contaminants. Part of this example describes metal contaminants such as Cu and Fe, although any manner of chemical contaminants can be evaluated in this way. The wafer 15 described is either a 100 mm or 150 mm wafer, although these examples apply to any size wafer. The wafer surface 16 is prepared by dipping in HF to remove oxides. The wafer 15 is then cleaned and partially dipped in the metal contaminant solution. The amount of solution remaining on the wafer 15, and the resulting concentration of contaminant on the wafer surface 16, is controlled by selecting dip coating parameters such as the extraction rate.

Partial dipping of the test wafer 15 is preferred to create a transition from clean to contaminated areas. Because the nvCPD signal is differential, the nvCPD sensor 12 detects changes on the wafer surface 16, as opposed to an absolute value relating to surface condition. This aspect of nvCPD sensors 12 is offset by the ability to rapidly image and detect localized contamination anywhere on the surface of the wafer 15.

Figure 7:
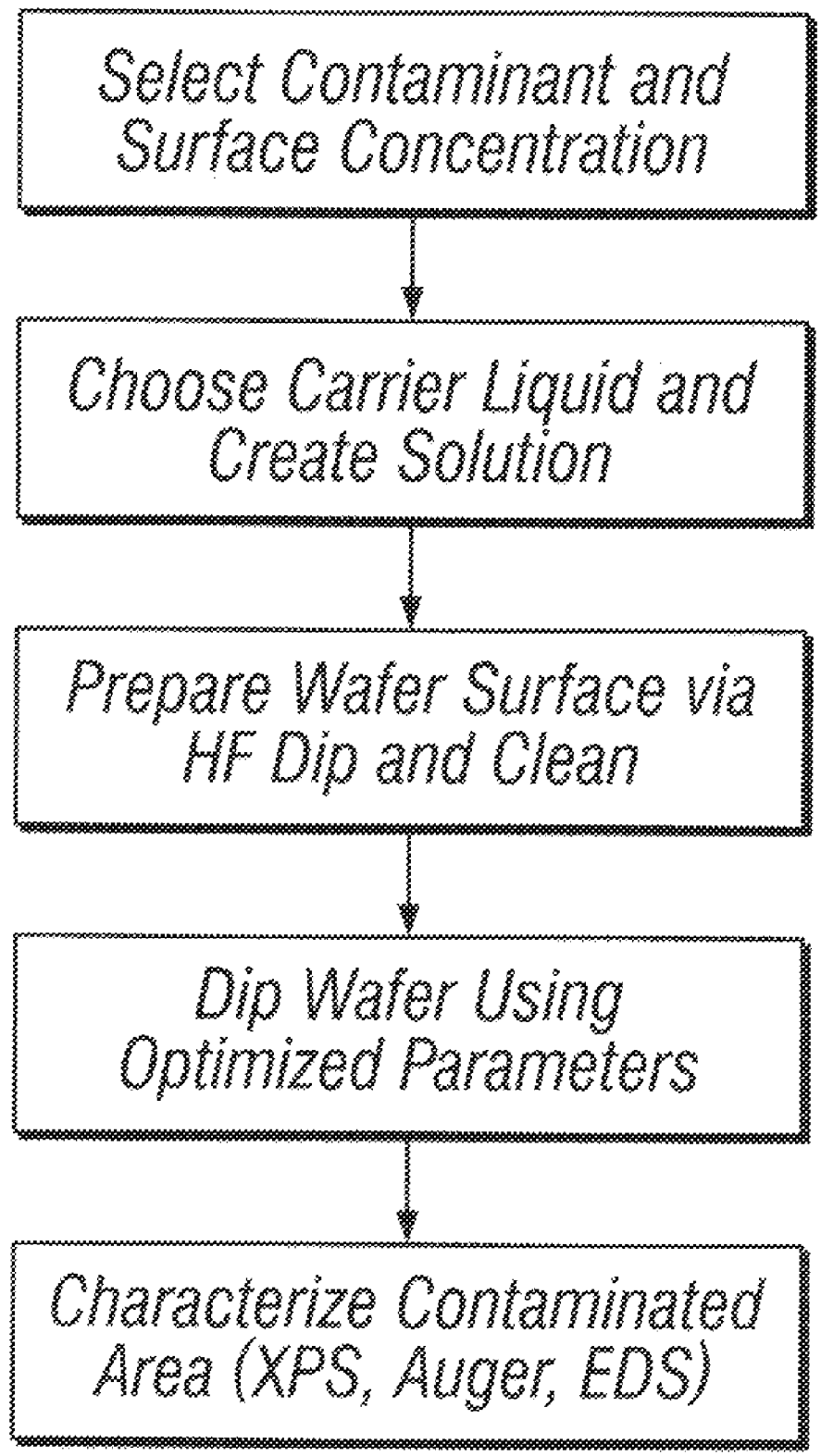
FIG. 7 illustrates steps for creating test wafers which are partially coated with known concentrations of contaminants.

After preparation, each test wafer 15 can be, if necessary, analyzed using an appropriate combination of XPS, Auger, and RBS (or other well known surface analysis methods) techniques to measure actual contaminant concentrations in the dipped areas of the wafer 15. Each step involved in the sample wafer preparation process is shown in FIG. 7. In a production line methodology, standards can be established correlating measure actual contamination concentration to nvCPD data for routine use.

After each sample wafer 15 is created, it can be imaged using a radially scanning nvCPD imaging system 10 constructed in accordance with the invention. As described before, FIGS. 8A and 8B show basic forms of the nvCPD imaging system 10, and FIG. 9 shows another flow diagram illustration of wafer processing. The system 10 employs the nvCPD sensor 12 mounted on the previously described three-axis positioning system 26. This positioning system 26 is used to position the nvCPD sensor 12 above the wafer surface 16 to be imaged, and to scan the nvCPD sensor 12 radially across the wafer surface. The wafer 15 is mounted on a spindle that rotates at high speed (1800 rpm) beneath the nvCPD sensor 12. The system 10 operates by acquiring multiple consecutive tracks of data as the nvCPD sensor 12 is stepped along the radius of rotation of the wafer 15.

Figure 10A:
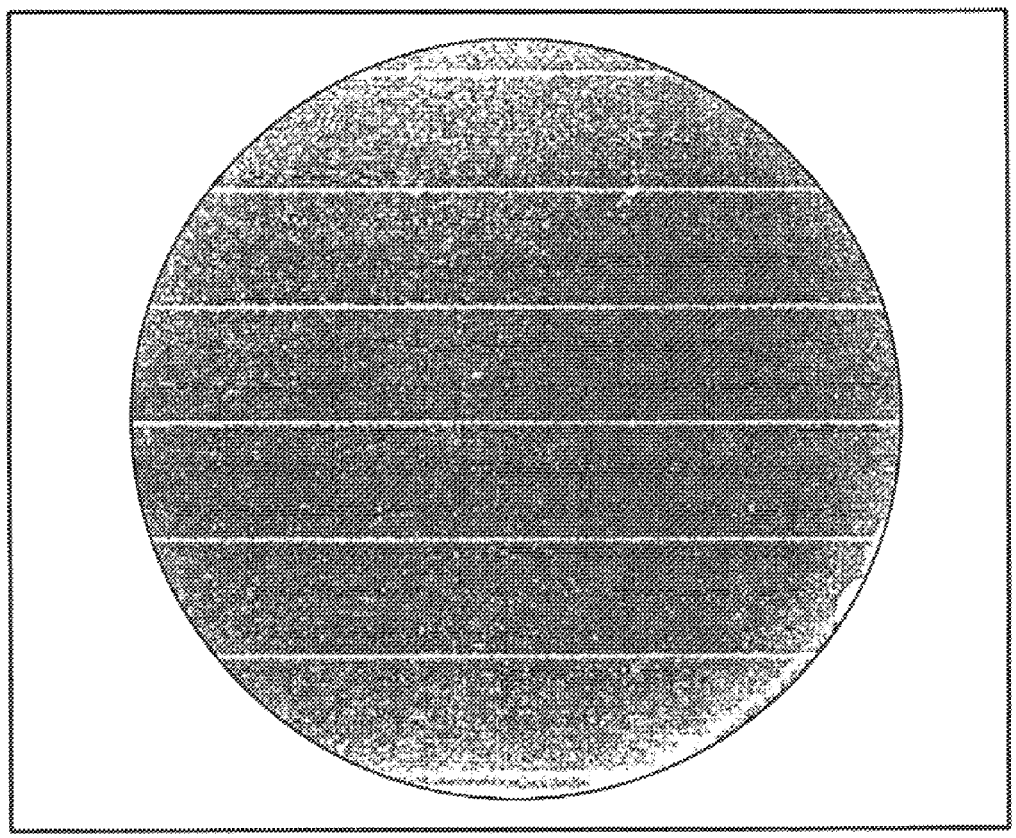
FIG. 10A illustrates an optical image of a 100 mm diameter silicon wafer after application of a vacuum pick-up device and FIG. 10B illustrates an nvCPD image of the wafer of FIG. 10A.
Figure 10B:
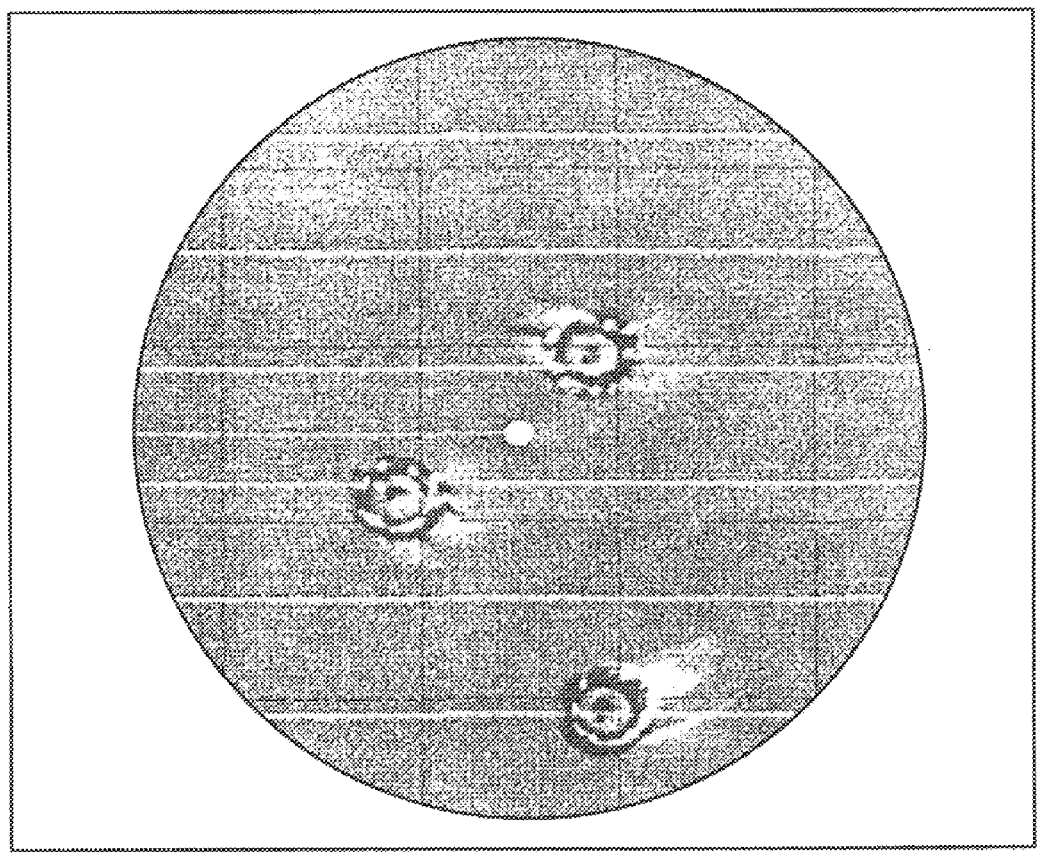

The imaging system 10 has been used for a variety of surface analysis experiments. FIGS. 10A, 10B, 11A, and 11B show sample wafer images that were generated using the nvCPD sensor 12 imaging for wafer inspection. The images show optical images in FIG. 10A and 11A and nvCPD images in FIG. 10B and 11B of a 100 mm form of the wafers 15. The first wafer 15 was cleaned, and then a small vacuum pick-up device was attached to the surface of the wafer 15 in three locations. The optical image of FIG. 10A shows no evidence of any change on the surface 16 of the wafer 15. The nvCPD image of FIG. 10B shows a very large signal at the locations where the pick-up device was applied. The nvCPD signal is believed to be the result of a small amount of residue left on the surface 16 by the pick-up device.

Figure 11A:
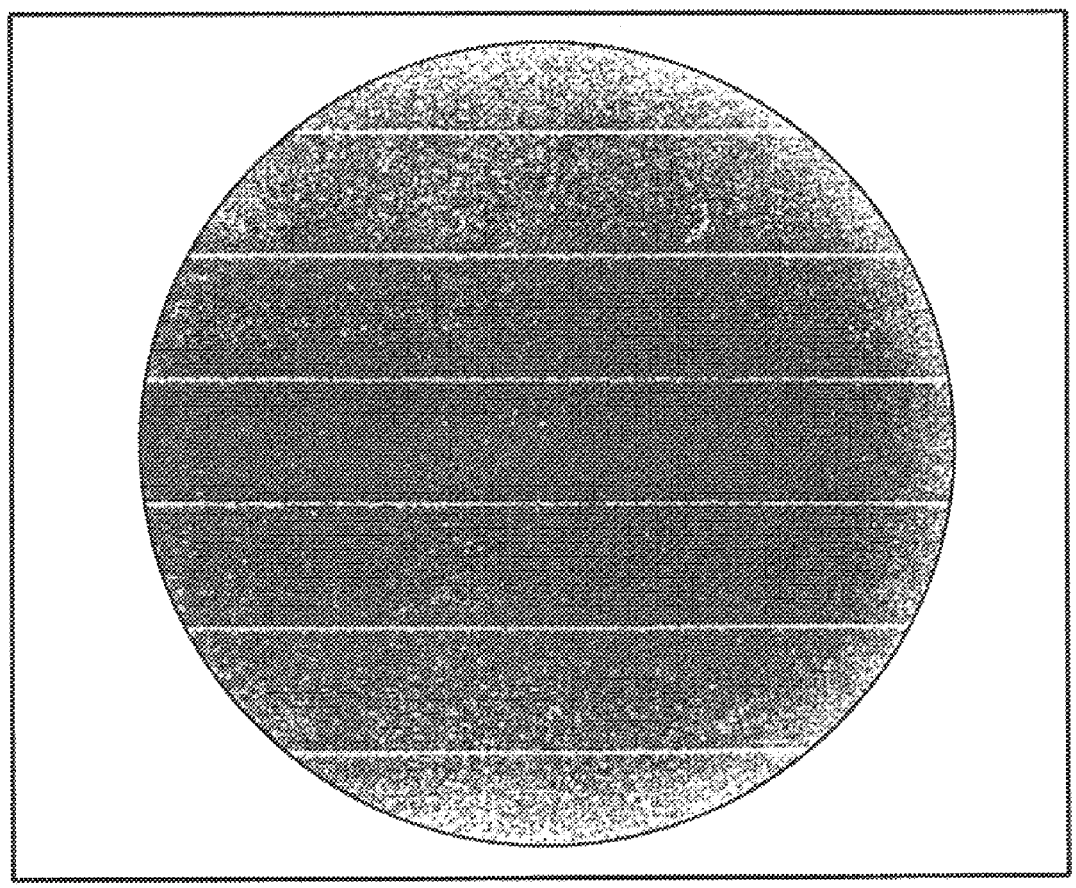
FIG. 11A illustrates an optical image of a second silicon wafer after applying alcohol while spinning the wafer and allowing the alcohol to dry and FIG. 11B is an nvCPD image of the same wafer of FIG. 11A.
Figure 11B:
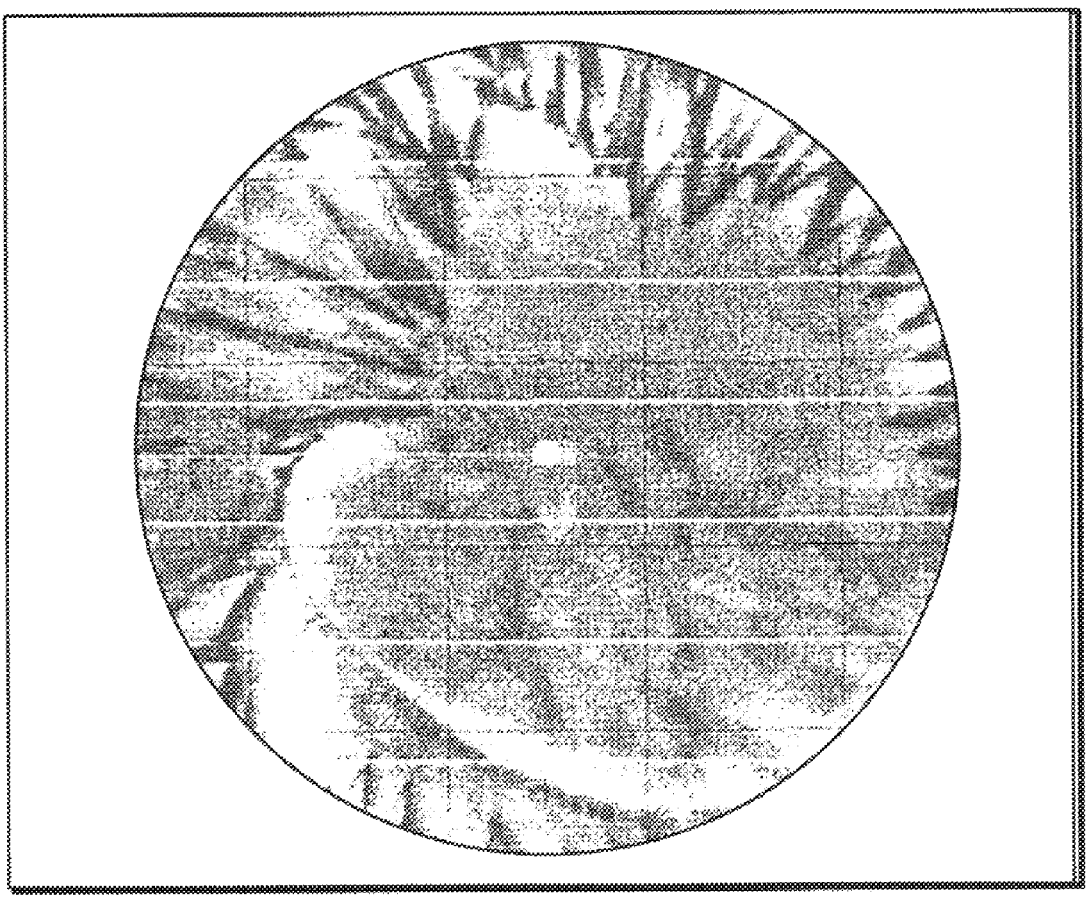

The second set of images in FIGS. 11A and 11B show a wafer 15 that has had alcohol spun-on and then dried. The resulting residue is not visible in the optical image FIG. 11A, but is clearly visible in the nvCPD image FIG. 11B. These images provide a clear demonstration of the usefulness of nvCPD sensor 12 for wafer inspection. Through careful measure of a full range of defect states and chemical constituents it is possible to correlate an image with a particular chemical state, defect, or combination thereof.

Figure 12A:
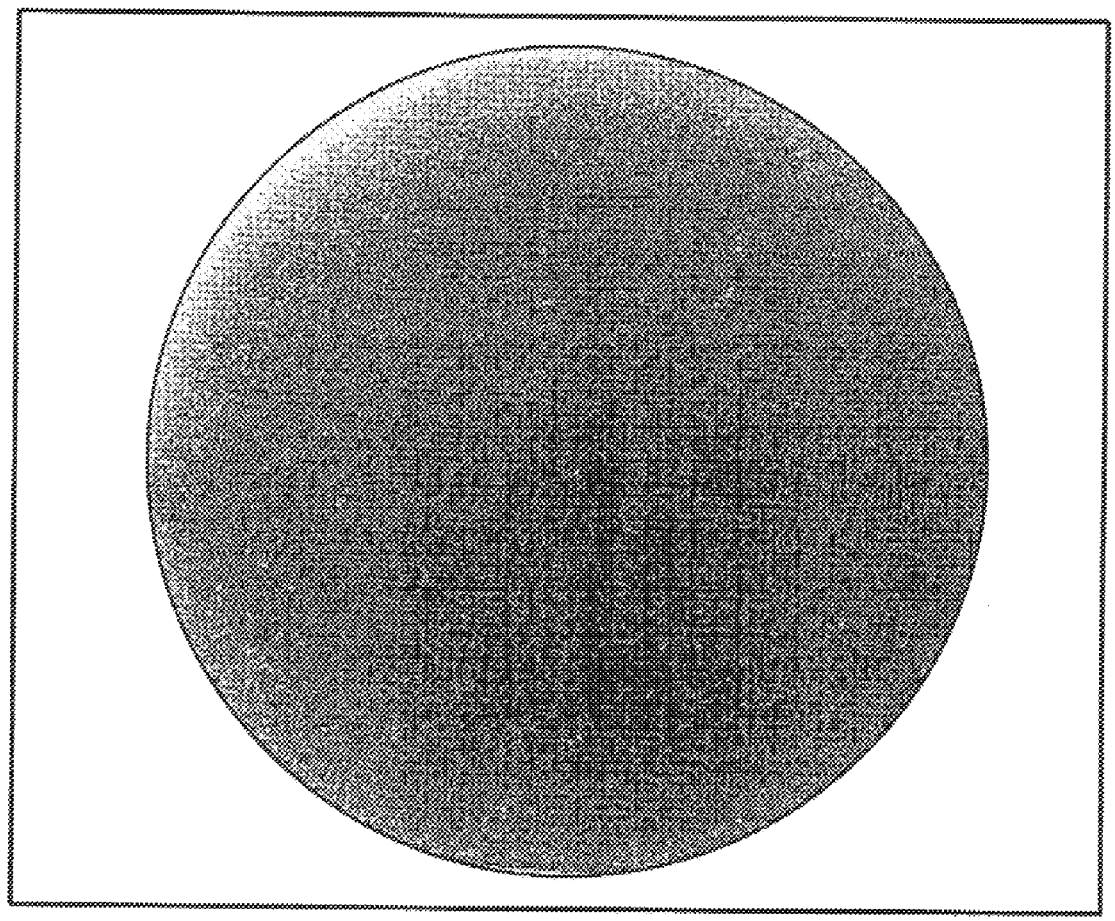
FIG. 12A illustrates an optical image of a silicon wafer after application of a latex glove mark and FIG. 12B is an nvCPD image of the same wafer of FIG. 12A.
Figure 12B:
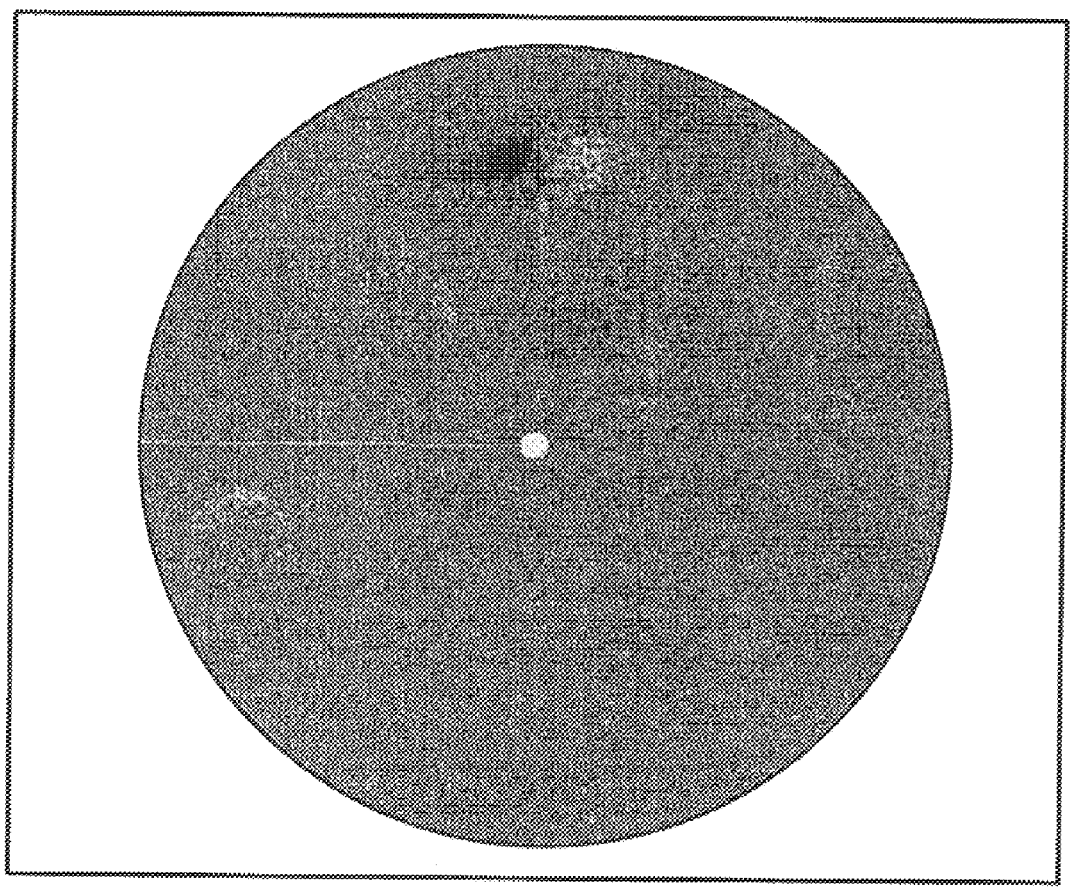
Figure 13A:
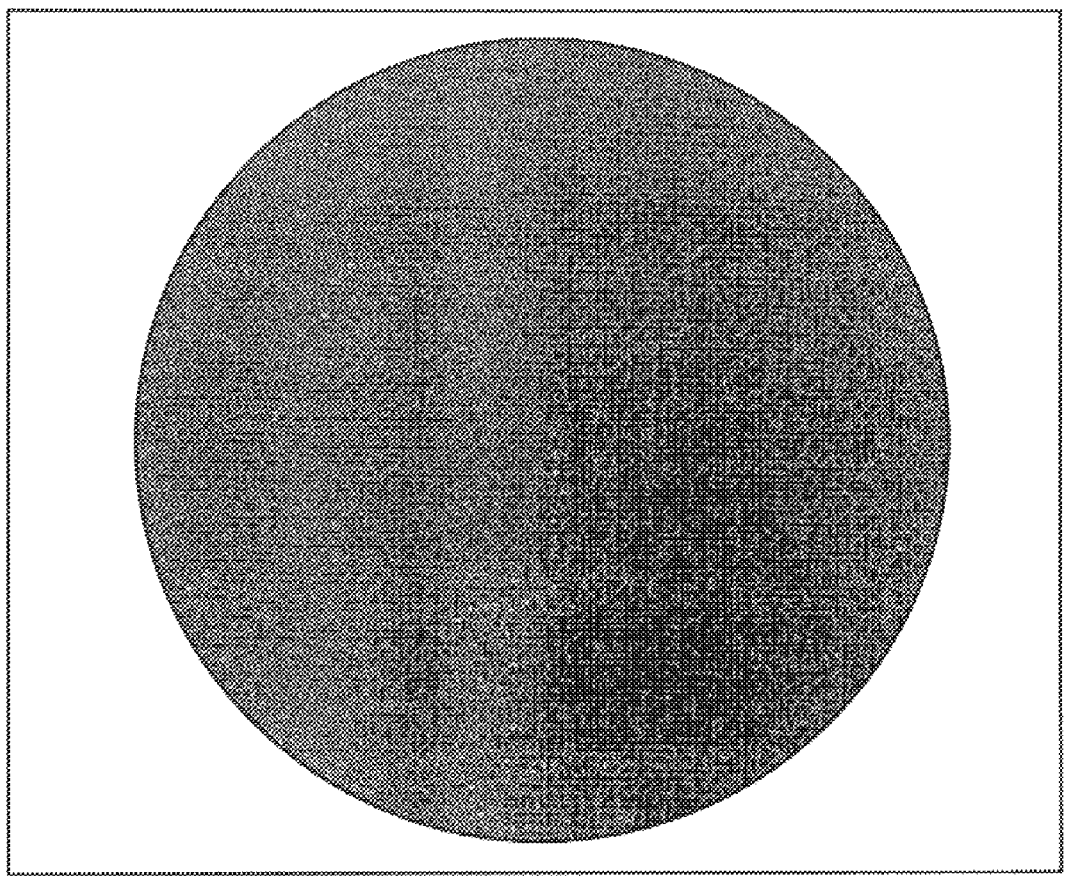
FIG. 13A illustrates an optical image of a silicon wafer having human fingerprints on the wafer and FIG. 13B illustrates an nvCPD image of the wafer of FIG. 13A.
Figure 13B:
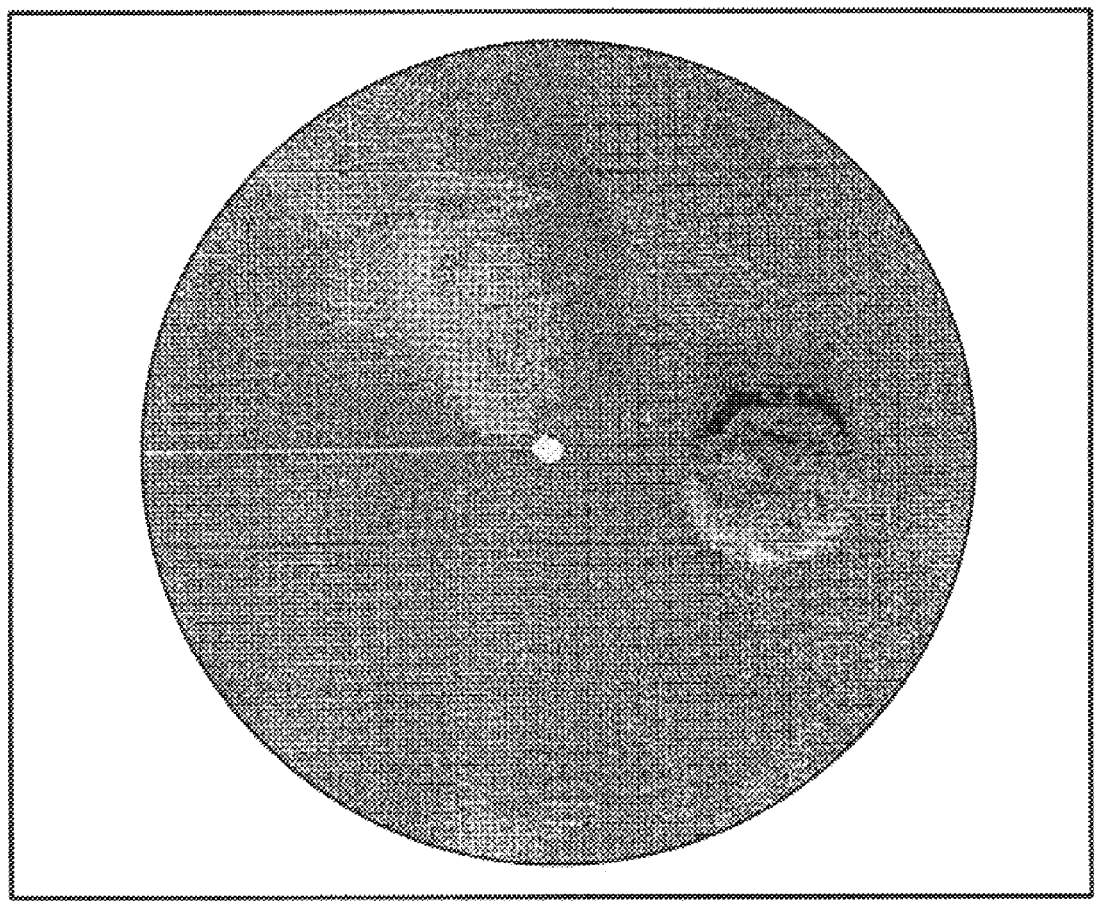
Figure 14:
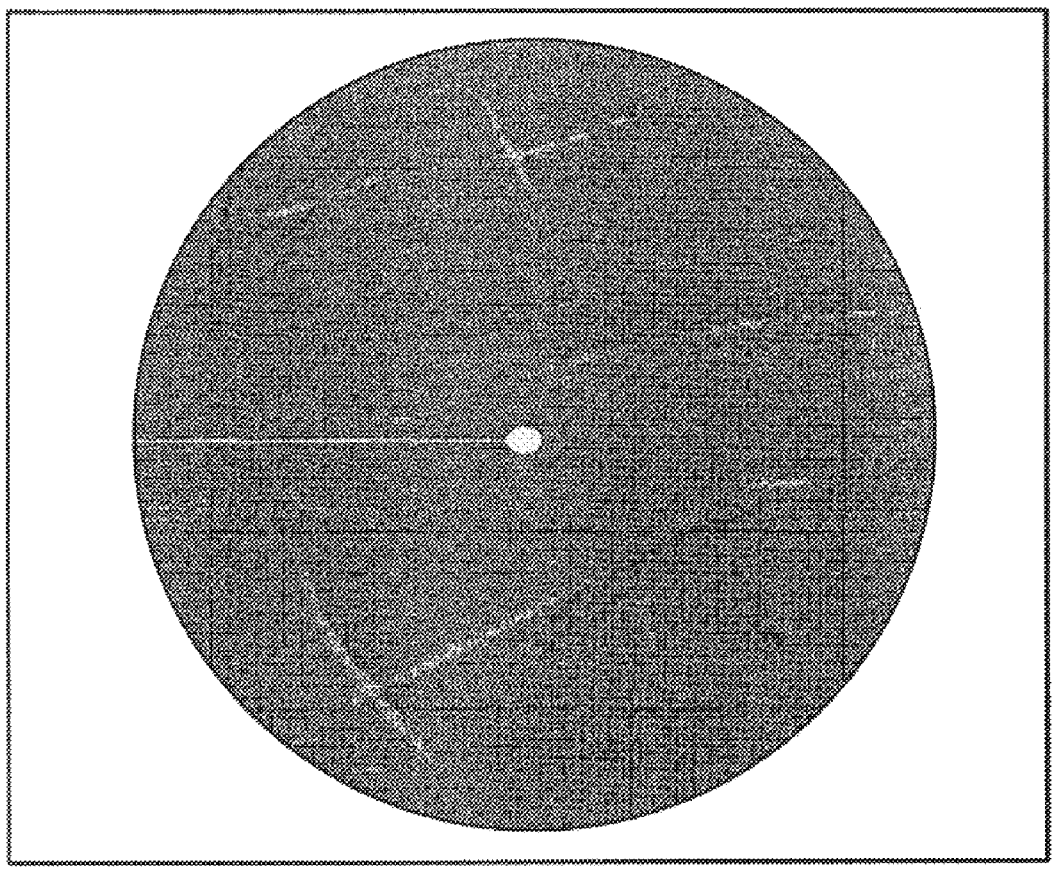
FIG. 14 illustrates an nvCPD image of a silicon wafer after brushing the wafer surface with a stainless steel tool.
Figure 15:
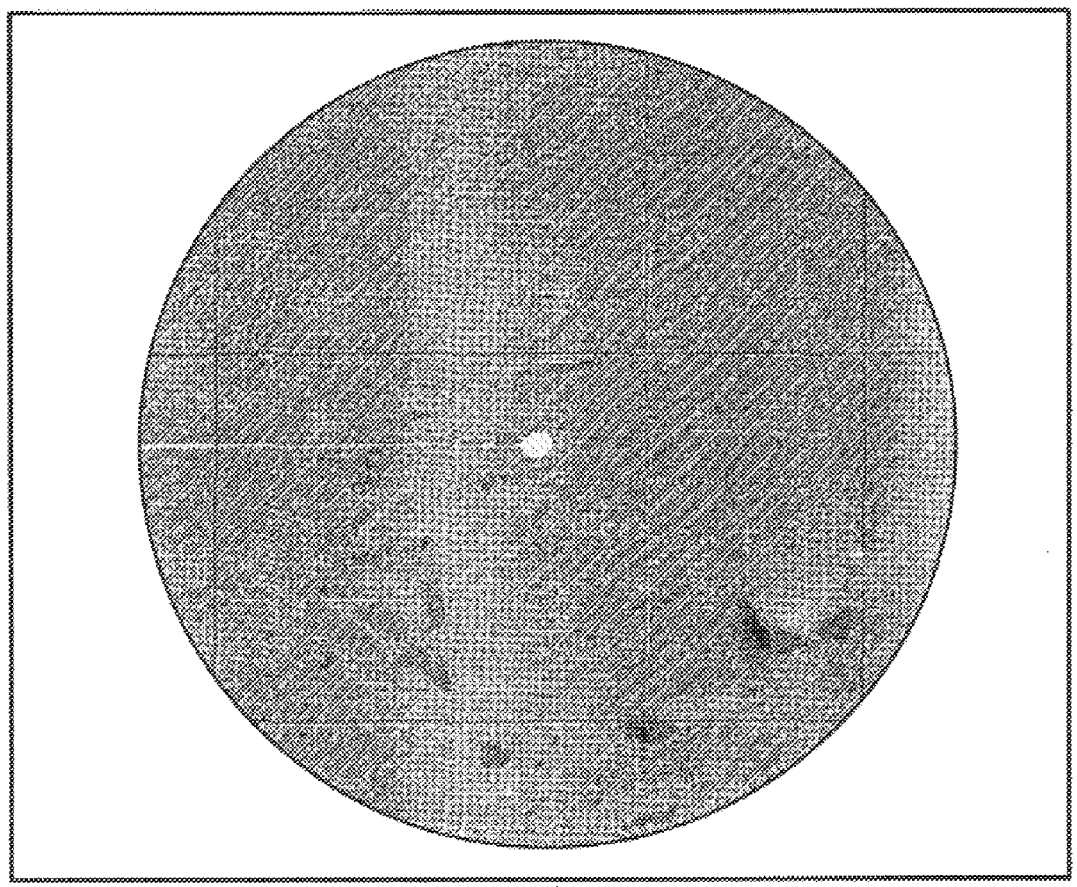
FIG. 15 illustrates an nvCPD image of a silicon wafer after pressing an aluminum fixture onto the wafer surface.

FIGS. 12A and 12B show, respectively, an optical image of latex glove marks and a nvCPD image of latex glove marks. FIGS. 13A and 13B show, respectively, an optical image of human fingerprints and an nvCPD image of the fingerprints. FIG. 14 shows a nvCPD image of a wafer 15 after brushing the wafer 15 with a stainless steel tool, and FIG. 15 shows a nvCPD image of the wafer 15 after pressing an aluminum fixture onto the wafer surface 16. All these example images were acquired using the nvCPD sensor 12 with the probe sensor tip 14 having a diameter of approximately 60 microns measured over a period of approximately 30 seconds.

While preferred embodiments of the invention have been shown and described, it will be clear to those skilled in the art that various changes and modifications can be made without departing from the invention in its broader aspects as set forth in the claims provided hereinafter.

The invention claimed is:

1. A method of inspecting a sample's surface with an inspection system, comprising the steps of:
   providing a sample having a surface;
   providing a non-vibrating contact potential probe;

scanning the sample's surface with the non-vibrating contact potential probe by causing relative motion between the non-vibrating contact potential probe and the sample's surface;

measuring contact potential difference between the sample's surface and the non-contact potential probe;

generating a first signal portion characteristic of a topographical feature of the sample's surface and further having a second signal portion representing chemical features of the sample's surface.

2. The method of inspecting a sample's surface of claim 1 further comprising the step of amplifying the topographical signal relative to the chemical signal.

3. The method of inspecting a sample's surface of claim 1 further comprising the step of biasing a portion of the inspection system.

4. The method of inspecting a sample's surface of claim 3 further comprising the steps of:

providing a negative bias voltage to a portion of the inspection system chosen from the group consisting of the non-vibrating contact potential difference probe, the sample, and combinations thereof;

providing a positive bias voltage of substantially equal but opposite charge as the negative bias voltage to the portion of the inspection system to which the first bias voltage was applied; and subtracting the negative bias signal from the positive bias signal.

5. The method of inspecting a sample's surface of claim 1, wherein the relative motion is accomplished by rotating the sample about a central axis with the probe tracing tracks of data at varying radii.

6. The method of inspecting a sample's surface of claim 5, further comprising the step of decreasing rotational velocity in proportion with the motion of the probe to provide the probe with substantially even data density.

7. The method of inspecting a sample's surface of claim 1 further comprising the step of providing a plurality of non-vibrating contact potential difference probes.

8. The method of inspecting a sample's surface of claim 7, wherein the plurality of probes are arranged in a linear array.

9. The method of inspecting a sample's surface of claim 7, wherein the plurality of probes are arranged in a two-dimensional array.

10. The method of inspecting a sample's surface of claim 7 further comprising the step of providing the plurality of probes at a plurality of heights.

11. The method of inspecting a sample's surface of claim 7 further comprising the step of providing a voltage bias to the plurality of probes.

12. The method of inspecting a sample's surface of claim 1, wherein the relative motion is provided by moving the non-contact potential difference probe with respect to the sample which is maintained substantially stationary.

13. The method of inspecting a sample's surface of claim 1, wherein the relative motion is provided by moving the sample with respect to the non-vibrating contact potential probe which is substantially stationary.

14. The method of inspecting a sample's surface of claim 1 further including the step of providing a height sensor.

15. The method of inspecting a sample's surface of claim 1, further including the step of calibrating the height of the non-vibrating contact potential difference probe to measurements made by the height sensor.

16. The method of inspecting a sample's surface of claim 1, wherein the step of calibrating the height of the non-vibrating contact potential difference probe to measurements made by the height sensor further comprises the steps of:

positioning the height sensor above a reference surface so that the distance between the reference surface and the height sensor is within a range of detection for the height sensor;

recording the height of the sensors as $z1$;

recording the height of the height sensor reading above a reference point as $h1$;

moving the non-vibrating contact potential sensor to a position above the reference point on the reference surface;

slowly moving the non-vibrating contact potential sensor down towards the reference surface while monitoring the level of the non-contact potential difference probe signal; and recording as $z2$ the height when the non-vibrating contact potential difference probe contacts the reference surface as indicated by a significant change in the output of the non-vibrating contact potential difference probe.

17. The method of inspecting a sample's surface of claim 16 further comprising the step of positioning the non-vibrating contact potential difference probe at a desired height of $h^*$ by the steps of:

positioning the height sensor above the surface so that the surface is within a measurement range of the height sensor;

recording this height as $z3$ and the height sensor reading as $h3$;

positioning the non-vibrating contact potential probe above the point $z3$; and adjusting the height to $z^* = z3 - (h3 - h1) - (z1 - z2) + h^*$, wherein the height of the non-vibrating contact potential difference probe is located above the surface of point $z3$ at height $h^*$.

18. The method of inspecting a sample's surface of claim 1, wherein the sample comprises an liquid crystal panel.

19. The method of inspecting a sample's surface of claim 1, wherein the sample comprises a semiconductor wafer.

20. A system for identifying features on the surface of a sample comprising:

a non-vibrating contact potential difference sensor;

a mechanism for causing relative motion between the sample and the non-vibrating contact potential difference sensor;

a mechanism for measuring contact potential difference between the sample and the non-vibrating contact potential probe;

a generated signal representing the contact potential difference; and a generated bias voltage applied to a portion of the system chosen from the group consisting of the sample, the non-vibrating contact potential probe, and combinations thereof.

21. The system for identifying features on the surface of a sample of claim 20 further comprising a plurality of non-vibrating contact potential probes.

22. The system for identifying features on the surface of a sample of claim 20 further comprising a height sensor.

23. The system for identifying features on the surface of a sample of claim 20, further comprising a voltage bias applied to a portion of the system.

24. A system for inspecting the surface of a sample comprising:
- a non-vibrating contact potential difference sensor;
- a chuck for rotating the sample about a central axis;
- the chuck having a variable speed control mechanism for changing rotational velocity in proportion with the motion of the probe to provide the probe with substantially even data density; and
- a source of data representing a contact potential difference between the non-vibrating contact potential difference sensor and the surface of the sample.

* * * * *